United States Patent [19]
Brown et al.

[11] Patent Number: 5,958,250
[45] Date of Patent: Sep. 28, 1999

[54] BLOOD PROCESSING SYSTEMS AND METHODS WHICH OPTICALLY DERIVE THE VOLUME OF PLATELETS CONTAINED IN A PLASMA CONSTITUENT

[75] Inventors: Richard I Brown, Northbrook; John T Foley, Wheeling; Kyungyoon Min, Gurnee; Mark Sahlin, Hainesville, all of Ill.

[73] Assignee: Baxter International Inc., Deerfield, Ill.

[21] Appl. No.: 08/896,665

[22] Filed: Jul. 18, 1997

Related U.S. Application Data

[63] Continuation-in-part of application No. 08/807,820, Feb. 26, 1997, Pat. No. 5,833,866, which is a continuation of application No. 08/472,748, Jun. 7, 1995, abandoned.

[51] Int. Cl.⁶ .................................................. B01D 17/12
[52] U.S. Cl. .......................... 210/745; 210/94; 210/96.1; 210/767; 494/10; 494/37; 604/5
[58] Field of Search ............................... 210/87, 94, 96.1, 210/143, 257.1, 645, 739, 745, 767, 85, 787, 789, 512.1; 604/4–6; 356/39; 494/1, 10, 37

[56] References Cited

U.S. PATENT DOCUMENTS

| | | | |
|---|---|---|---|
| 3,727,066 | 4/1973 | Louderback et al. | |
| 3,752,995 | 8/1973 | Liedholz | |
| 4,468,219 | 8/1984 | George et al. | 604/66 |
| 4,810,090 | 3/1989 | Boucher et al. | 356/39 |
| 4,828,716 | 5/1989 | McEwen et al. | 210/745 |
| 5,104,526 | 4/1992 | Brown et al. | 210/94 |
| 5,316,666 | 5/1994 | Brown et al. | 210/85 |
| 5,316,667 | 5/1994 | Brown et al. | 210/85 |
| 5,437,598 | 8/1995 | Antwiler | 494/1 |
| 5,478,479 | 12/1995 | Herrig | 210/745 |
| 5,494,592 | 2/1996 | Latham et al. | 604/4 |
| 5,496,265 | 3/1996 | Langley et al. | 604/5 |
| 5,573,678 | 11/1996 | Brown et al. | 210/782 |
| 5,605,842 | 2/1997 | Langley et al. | 436/177 |
| 5,611,997 | 3/1997 | Langley et al. | 422/73 |
| 5,637,082 | 6/1997 | Pages et al. | 604/6 |
| 5,639,382 | 6/1997 | Brown | 210/739 |
| 5,656,163 | 8/1997 | Brown | 210/94 |
| 5,658,240 | 8/1997 | Urdahl et al. | 604/5 |
| 5,681,273 | 10/1997 | Brown | 604/6 |
| 5,730,883 | 3/1998 | Brown | 210/739 |
| 5,769,811 | 6/1998 | Stacey et al. | 604/4 |
| 5,792,372 | 8/1998 | Brown et al. | 604/5 |

OTHER PUBLICATIONS

Liles et al, A comparative trial of granulocyte–colony–stimulating factor and dexamethasone, separately and in combination for the mobilzation of neutrophils in the peripheral blood of normal volunteers, Transfusion, vol. 37, Mar. 1997.

Dumont et al., Enhanced Flow Cytometric Method for Counting Very Low Numbers of White Cells in Platelet Products, Cytometry, 26:311–318(1996).

*Primary Examiner*—Joseph W. Drodge
*Attorney, Agent, or Firm*—Bradford R.L. Price; Denise M. Serewicz; Daniel D. Ryan

[57] ABSTRACT

Blood processing systems and methods separate blood into constituents including a plasma constituent that includes a platelet volume. The systems and methods detect the optical density of the plasma constituent and generate a first output indicative of the optical density. A processing element integrates the first output relative to the volume of plasma constituent and generates an integrated output. The integrated output correlates to the platelet volume. A second processing element generates a third output based, at least in part, upon the integrated output, which comprises parameters for storing the platelet volume.

30 Claims, 14 Drawing Sheets

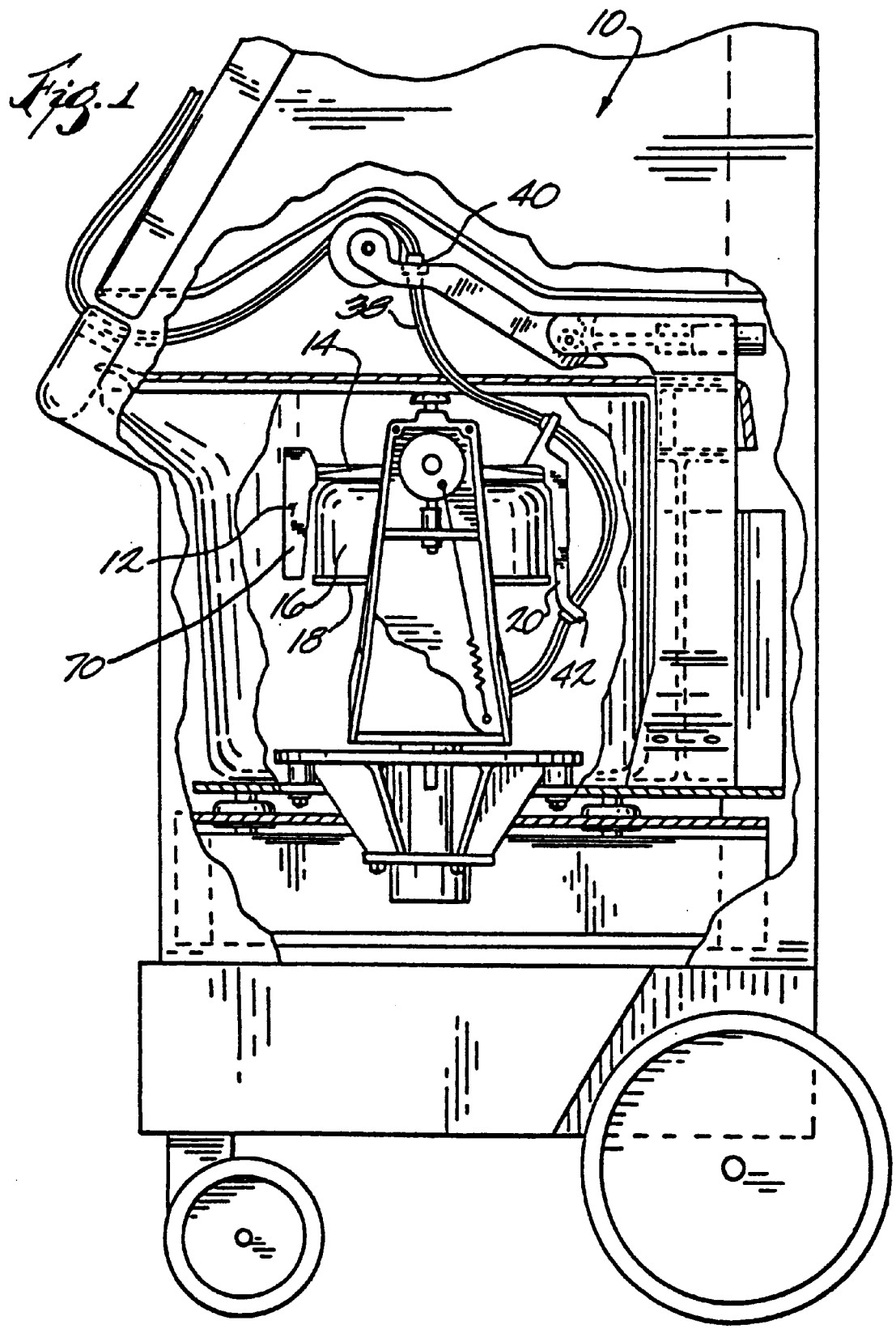

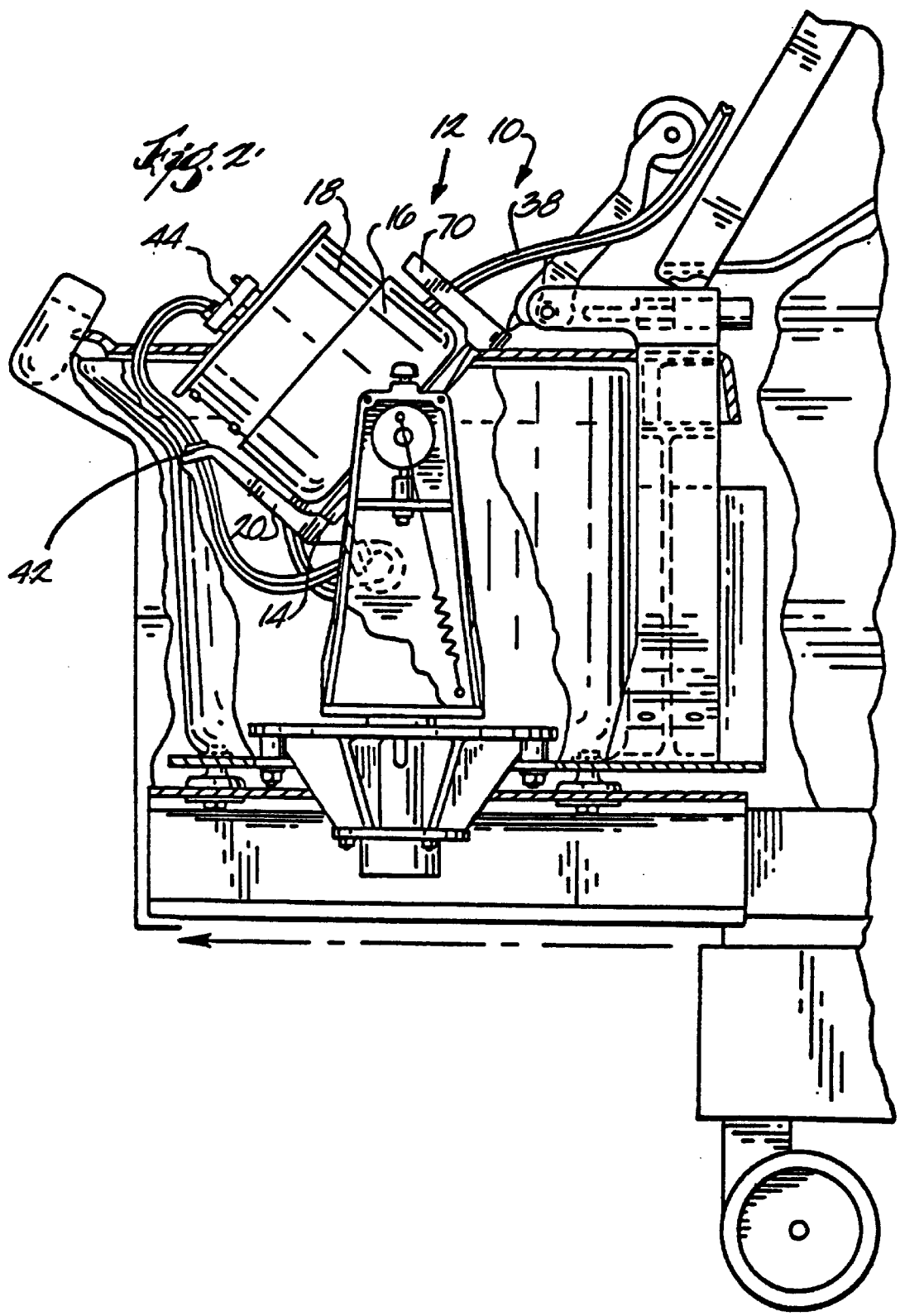

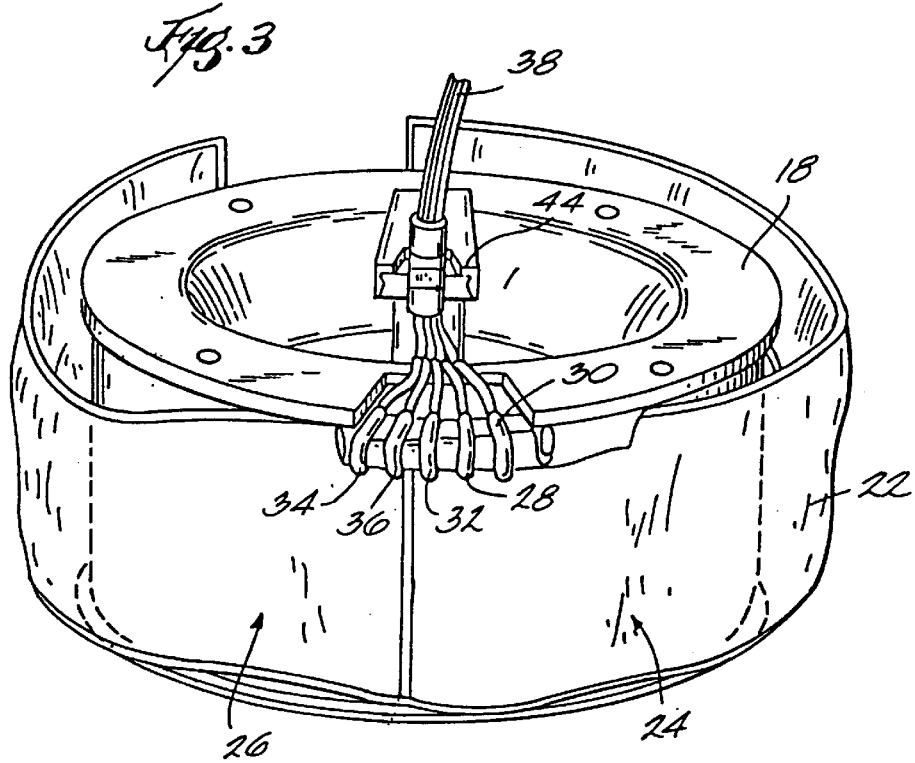
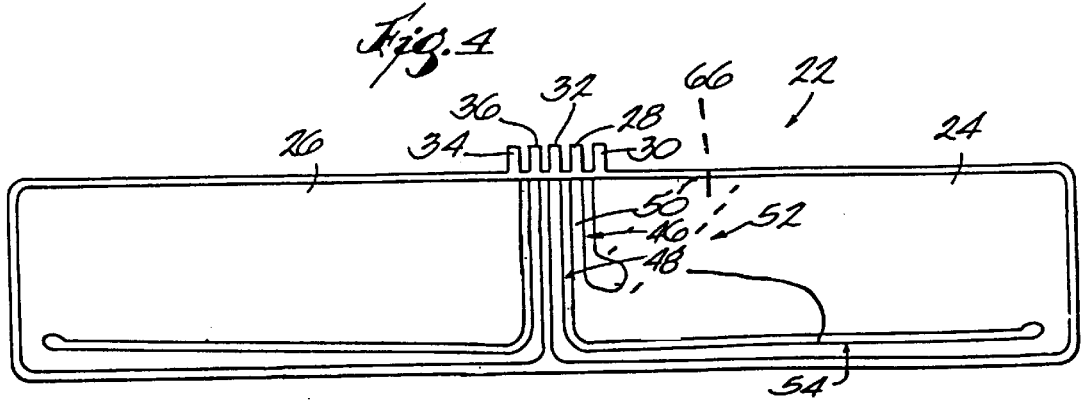

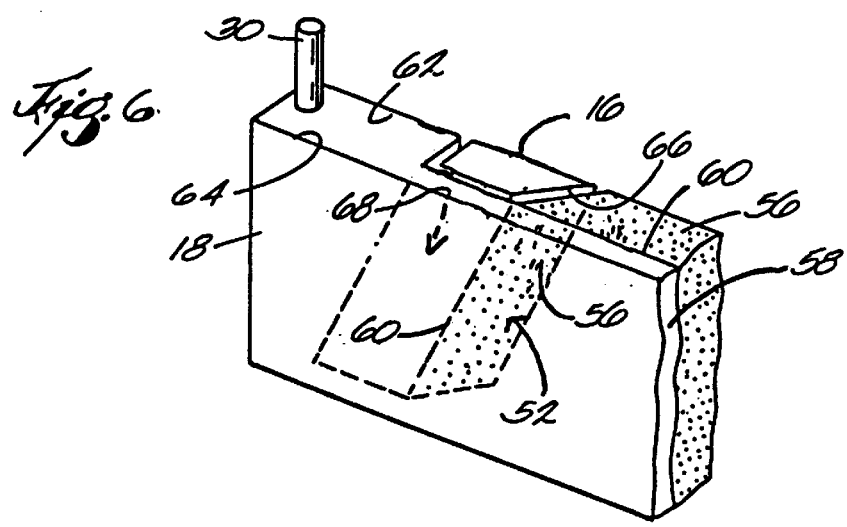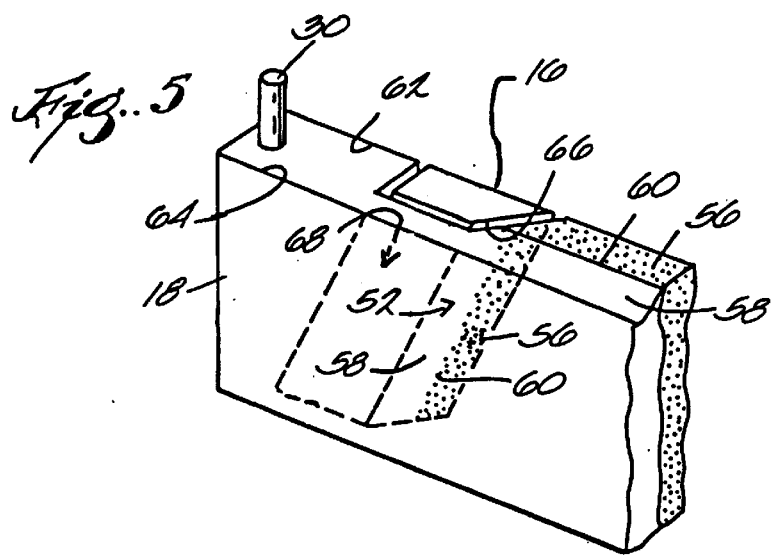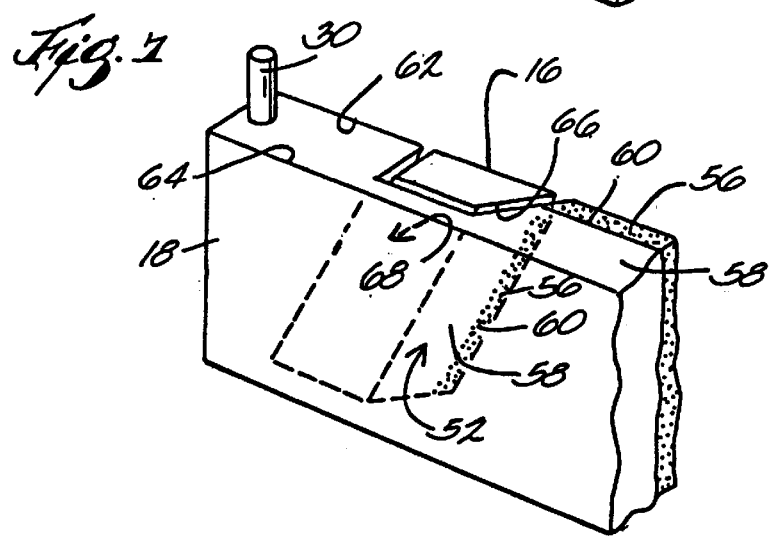

BLOOD PROCESSING SYSTEMS AND METHODS WHICH OPTICALLY DERIVE THE VOLUME OF PLATELETS CONTAINED IN A PLASMA CONSTITUENT

RELATED APPLICATION

This application is a continuation-in-part of U.S. patent application Ser. No. 08/807,820, filed Feb. 26, 1997, now U.S. Pat. No. 5,833,866 and entitled "Blood Collection Systems and Methods Which Derive Instantaneous Blood Component Yield Information During Blood Processing," which is a continuation of U.S. patent application Ser. No. 08/472,748, filed Jun. 7, 1995 of the same title (now abandoned).

FIELD OF THE INVENTION

The invention relates to centrifugal processing systems and apparatus.

BACKGROUND OF THE INVENTION

Today, people routinely separate whole blood by centrifugation into its various therapeutic components, such as red blood cells, platelets, and plasma.

Certain therapies transfuse large volumes of blood components. For example, some patients undergoing chemotherapy require the transfusion of large numbers of platelets on a routine basis. Manual blood bag systems simply are not an efficient way to collect these large numbers of platelets from individual donors.

On line blood separation systems are today used to collect large numbers of platelets to meet this demand. On line systems perform the separation steps necessary to separate concentration of platelets from whole blood in a sequential process with the donor present. On line systems establish a flow of whole blood from the donor, separate out the desired platelets from the flow, and return the remaining red blood cells and plasma to the donor, all in a sequential flow loop.

Large volumes of whole blood (for example, 2.0 liters) can be processed using an on line system. Due to the large processing volumes, large yields of concentrated platelets (for example, $4 \times 10^{11}$ platelets suspended in 200 ml of fluid) can be collected. Moreover, since the donor's red blood cells are returned, the donor can donate whole blood for on line processing much more frequently than donors for processing in multiple blood bag systems.

Nevertheless, a need still exists for further improved systems and methods for collecting cellular-rich concentrates from blood components in a way that lends itself to use in high volume, on line blood collection environments, where higher yields of critically needed cellular blood components like platelets can be realized.

As the operational and performance demands upon such fluid processing systems become more complex and sophisticated, the need exists for automated process controllers that can gather and generate more detailed information and control signals to aid the operator in maximizing processing and separation efficiencies.

SUMMARY OF THE INVENTION

The invention provides blood processing systems and methods which separate blood into constituents including a plasma constituent having an optical density. The systems and methods convey a volume of the plasma constituent through an outlet path, while detecting the optical density of the plasma constituent. The systems and methods generate a first output indicative of the detected optical density. The systems and methods integrate the first output relative to the volume of plasma constituent conveyed to generate an integrated output. The integrated output correlates to the platelet volume carried in the plasma constituent and obviates the need to otherwise obtain the platelet volume by off line counting and sizing techniques.

In a preferred embodiment, the plasma constituent includes a lipid content. In this embodiment, the systems and methods adjust the first output in proportion to the lipid content.

In a preferred embodiment, the systems and methods generate a third output based, at least in part, upon the integrated output. In a preferred embodiment, the third output comprises parameters for storing the platelet volume contained within the plasma constituent. For example, the third output can include a value representing the number of selected storage containers to be used for the platelet volume, or a value representing the recommended volume of storage medium for the platelet volume.

In a preferred embodiment, the storage medium is plasma. In recommending the storage parameters for platelets, the systems and methods take into account the buffering effect of bicarbonate in the plasma to keep the pH at a level to sustain platelet viability during storage. The systems and methods also take into effect the partial pressure of oxygen of platelets to keep the platelets outside an anaerobic state during storage. In this way, the systems and methods derive optimal storage conditions to sustain platelets during the expected storage period.

The various aspects of the invention are especially well suited for on line blood separation processes.

Features and advantages of the inventions are set forth in the following Description and Drawings, as well as in the appended Claims.

BRIEF DESCRIPTION OF THE DRAWINGS

FIG. 1 is a side elevation view, with portions broken away and in section, of a blood processing system comprising a centrifuge with an interface detection system, which embodies features of the invention, the bowl and spool of the centrifuge being shown in their operating position;

FIG. 2 is a side elevation view, with portions broken away and in section, of the centrifuge shown in FIG. 1, with the bowl and spool of the centrifuge shown in their upright position for receiving a blood processing chamber;

FIG. 3 is a top perspective view of the spool of the centrifuge shown in FIG. 2, in its upright position and carrying the blood processing chamber;

FIG. 4 is a plan view of the blood processing chamber shown in FIG. 3, out of association with the spool;

FIG. 5 is an enlarged perspective view of the interface ramp carried by the centrifuge in association with the blood processing chamber, showing the centrifugally separated red blood cell layer, plasma layer, and interface within the chamber when in a desired location on the ramp;

FIG. 6 is an enlarged perspective view of the interface ramp shown in FIG. 5, showing the red blood cell layer and interface at an undesired high location on the ramp;

FIG. 7 is an enlarged perspective view of the interface ramp shown in FIG. 5, showing the red blood cell layer and interface at an undesired low location on the ramp;

Figure 8:
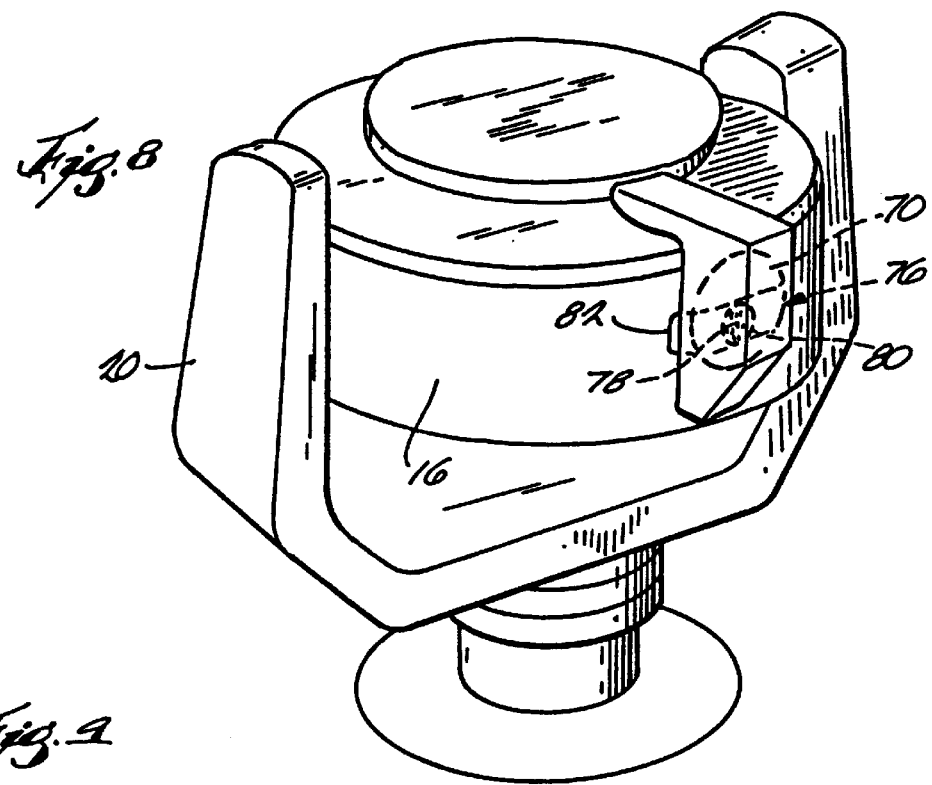
FIG. 8 is a side perspective view of the bowl and spool of the centrifuge when in the operating position, showing the viewing head, which forms a part of the interface controller, being carried by the centrifuge to view the interface ramp during rotation of the bowl.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIGS. 1 and 2 show a blood processing system 10, which incorporates an interface controller 12 that embodies features of the invention. The invention is described in the context of blood processing, because it is well suited for use in this environment. Still, it should be appreciated that use of the invention is not limited to blood processing. The features of the invention can be used in association with any system in which materials that can be optically differentiated are handled.

A. The Centrifuge

The system 10 includes a centrifuge 14 used to centrifugally separate blood components. In the illustrated embodiment, the centrifuge 14 separates whole blood to harvest red blood cells (RBC), platelet concentrate (PC), and platelet-poor plasma (PPP). The centrifuge 14 can also be used to harvest mononuclear cells and granulocytes from blood.

The centrifuge 14 is of the type shown in U.S. Pat. No. 5,316,667, which is incorporated herein by reference. The centrifuge comprises a bowl 16 and a spool 18. The bowl 16 and spool 18 are pivoted on a yoke 20 between an upright position, as FIG. 2 shows, and a suspended position, as FIG. 1 shows.

When upright, the spool 18 can be opened by movement at least partially out of the bowl 16, as FIG. 2 shows. In this position, the operator wraps a flexible blood processing chamber 22 (see FIG. 3) about the spool 18. Closure of the spool 18 and bowl 16 encloses the chamber 22 for processing. When closed, the spool 18 and bowl 16 are pivoted into the suspended position for rotation about an axis.

B. The Blood Processing Chamber

The blood processing chamber 22 can be variously constructed. FIG. 4 shows a representative preferred embodiment.

The chamber 22 shown in FIG. 4 provides multi-stage processing. A first stage 24 separates WB into RBC and platelet-rich plasma (PRP). A second stage 26 separates the PRP into PC and PPP.

As FIGS. 3 and 4 best show, a port 28 conveys WB into the first stage 24. Ports 30 and 32, respectively, convey PRP and RBC from the first stage 24. RBC is returned to the donor. A port 34 conveys PRP into the second stage 26. A port 36 conveys PPP from the second stage 26, leaving PC in the second stage 26 for resuspension and transfer to one or more storage containers. The ports 28, 30, 32, 34, and 36 are arranged side-by-side along the top transverse edge of the chamber 22.

As FIGS. 1 and 3 best show, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the suspended spool 18 and bowl 16. A holder 42 on the yoke 20 rotates the mid-portion of the umbilicus 38 at a first (one omega) speed about the suspended spool 18 and bowl 16. Another holder 44 (see FIG. 2) rotates the lower end of the umbilicus 38 at a second speed twice the one omega speed (the two omega speed), at which the suspended spool 18 and bowl 16 also rotate. This known relative rotation of the umbilicus 38 keeps it untwisted, in this way avoiding the need for rotating seals.

As FIG. 4 shows, a first interior seal 46 is located between the PRP collection port 30 and the WB inlet port 28. A second interior seal 48 is located between the WB inlet port 28 and the RBC collection port 32. The interior seals 46 and 48 form a WB inlet passage 50 and a PRP collection region 52 in the first stage 24. The second seal 48 also forms a RBC collection passage 54 in the first stage 24.

The WB inlet passage 50 channels WB directly into the circumferential flow path immediately next to the PRP collection region 52. As shown in FIG. 5, the WB separates into an optically dense layer 56 of RBC, which forms as RBC move under the influence of centrifugal force toward the high-G wall 62. The movement of RBC 56 displaces PRP radially toward the low-G wall 64, forming a second, less optically dense layer 58.

Centrifugation of WB also forms an intermediate layer 60, also called the interface, which constitutes the transition between the formed cellular blood components and the liquid plasma component. RBC typically occupy this transition region. White blood cells may also occupy this transition region.

Platelets, too, can leave the PRP layer 58 and settle on the interface 60. This settling action occurs when the radial velocity of the plasma near the interface 60 is not enough to keep the platelets suspended in the PRP layer 58. Lacking sufficient radial flow of plasma, the platelets fall back and settle on the interface 60. Larger platelets (greater than about 30 femtoliters) are particularly subject to settling on the interface 60. However, the closeness of the WB inlet region 50 to the PRP collection region 52 in the chamber 22 shown in FIG. 4 creates strong radial flow of plasma into the PRP collection region 52. The strong radial flow of plasma lifts platelets, large and small, from the interface 60 and into the PRP collection region 52.

Further details of the separation chamber 22 are not material to the invention and can be found in U.S. Pat. No. 5,316,667, previously mentioned.

C. The Interface Controller

As FIG. 5 shows, a ramp 66 extends from the high-G wall 62 of the bowl 16 at an angle across the PRP collection region 52. The angle, measured with respect to the axis of the PRP collection port 30 is preferably about 30°. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the PRP collection port 30 are not material to the invention. They can be found in copending U.S. patent application Ser. No. 08/472,561, filed Jun. 7, 1995, now U.S. Pat. No. 5,632,893, and entitled "Enhanced Yield Blood Processing System with Angled Interface Control Surface," which is incorporated herein by reference.

The ramp 66 forms a tapered wedge that restricts the flow of fluid toward the PRP collection port 30. The top edge of the ramp 66 extends to form a constricted passage 68 along the low-G wall 64. PRP must flow through the constricted passage 68 to reach the PRP collection port 30.

As FIG. 5 shows, the ramp 66 diverts the fluid flow along the high-G wall 62. This flow diversion changes the orientation of the interface 60 between the RBC layer 56 and the PRP layer 58 within the PRP collection region 52. The ramp 66 thereby displays the RBC layer 56, PRP layer 58, and interface 60 for viewing through the low-G wall 64 of the chamber 22.

The interface controller 12 includes a viewing head 70 (see FIGS. 1 and 8) carried on the yoke 20. The viewing head 70 is oriented to optically view the transition in optical density between the RBC layer 56 and the PRP layer 58 on the ramp 66. The interface controller 12 also includes a processing element 72 (see FIGS. 11 and 13), which analyzes the optical data obtained by the viewing head 70 to derive the location of the interface 60 on the ramp 66 relative to the constricted passage 68.

The location of the interface 60 on the ramp 66 can dynamically shift during blood processing, as FIGS. 6 and 7 show. The interface controller 12 includes a command element 74 (see FIGS. 11 and 13), which varies the rate at which PRP is drawn from the chamber 22 to keep the interface 60 at a prescribed location on the ramp 66 (which FIG. 5 shows).

Maintaining the interface 60 at a prescribed location on the ramp 66 is important. If the location of the interface 60 is too high (that is, if it is too close to the constricted passage 68 leading to the PRP collection port 30, as FIG. 6 shows), RBC, and, if present, white blood cells can spill over and into the constricted passage 68, adversely affecting the quality of PRP. On the other hand, if the location of the interface 60 is too low (that is, if it resides too far away from the constricted passage 68, as FIG. 7 shows), the fluid dynamics advantageous to effective platelet separation can be disrupted. Furthermore, as the distance between the interface 60 and the constricted passage 68 increases, the difficulty of drawing larger platelets into the PRP flow increases. As a result, a distant interface location results in collection of only the smallest platelets, and overall platelet yield will, as a consequence, be poor.

(1) The Interface Viewing Head

Figure 9:
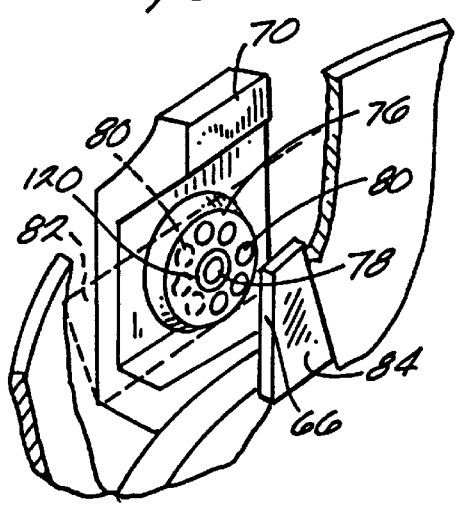
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
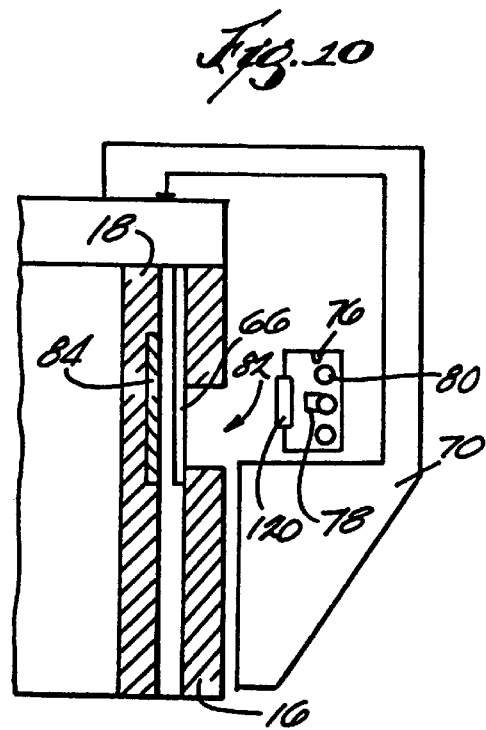
FIG. 10 is a side section view of the bowl, spool, and viewing head when the viewing head is aligned with the interface ramp.

Referring to FIGS. 8 to 10, the viewing head 70, carried by the yoke 20, includes a light source 76, which emits light that is absorbed by RBC. In the illustrated and preferred embodiment, the light source 76 includes a circular array of red light emitting diodes 80. of course, other wavelengths absorbed by RBC, like green or infrared, could be used.

In the illustrated embodiment, seven light emitting diodes 80 comprise the light source 76. More diodes 80 may be used, or fewer diodes 80 can be used, depending upon the optical characteristics desired.

The viewing head 70 also includes a light detector 78 (see FIGS. 9 and 10), which is mounted adjacent to the light source 76. In the illustrated and preferred embodiment, the light detector 78 comprises a PIN diode detector, which is located generally in the geometric center of the circular array of light emitting diodes 80.

The yoke 20 and viewing head 70 rotate at a one omega speed, as the spool 18 and bowl 16 rotate at a two omega speed. The light source 76 directs light onto the rotating bowl 16. In the illustrated embodiment (see FIG. 8), the bowl 16 is transparent to the light emitted by the source 76 only in the region 82 where the bowl 16 overlies the interface ramp 66. In the illustrated embodiment, the region 82 comprises a window cut out in the bowl 16. The remainder of the bowl 16 that lies in the path of the viewing head 70 comprises a light absorbing material.

The interface ramp 66 is made of a light transmissive material. The light from the source 76 will thereby pass through the transparent region 82 of the bowl 16 and the ramp 66 every time the rotating bowl 16 and viewing head 70 align. The spool 18 may also carry a light reflective material 84 behind the interface ramp 66 to enhance its reflective properties. The spool 18 reflects incoming light received from the source 76 out through the transparent region 82 of the bowl 16, where it is sensed by the detector 78. In the illustrated embodiment, light passing outward from the source 76 and inward toward the detector 78 passes through a focusing lens 120 (shown in FIGS. 9 and 10), which forms a part of the viewing head 70.

The arrangement just described optically differentiates the reflective properties of the interface ramp 66 from the remainder of the bowl 16. This objective can be achieved in other ways. For example, the light source 76 could be gated on and off with the arrival and passage of the ramp 66 relative to its line of sight. As another example, the bowl 16 outside the transparent region 82 could carry a material that reflects light, but at a different intensity than the reflective material 84 behind the interface ramp 66.

As the transparent interface region 82 of the bowl 16 comes into alignment with the viewing head 70, the detector 78 will first sense light reflected through the plasma layer 58 on the ramp 66. Eventually, the RBC layer 56 adjacent the interface 60 on the ramp 66 will enter the optical path of the viewing head 70. The RBC layer 56 absorbs light from the source 76 and thereby reduces the previously sensed intensity of the reflected light. The intensity of the reflected light sensed by the detector 78 represents the amount of light from the source 76 that is not absorbed by the RBC layer 56 adjacent to the interface 60.

(2) The Interface Processing Element

Figure 11:
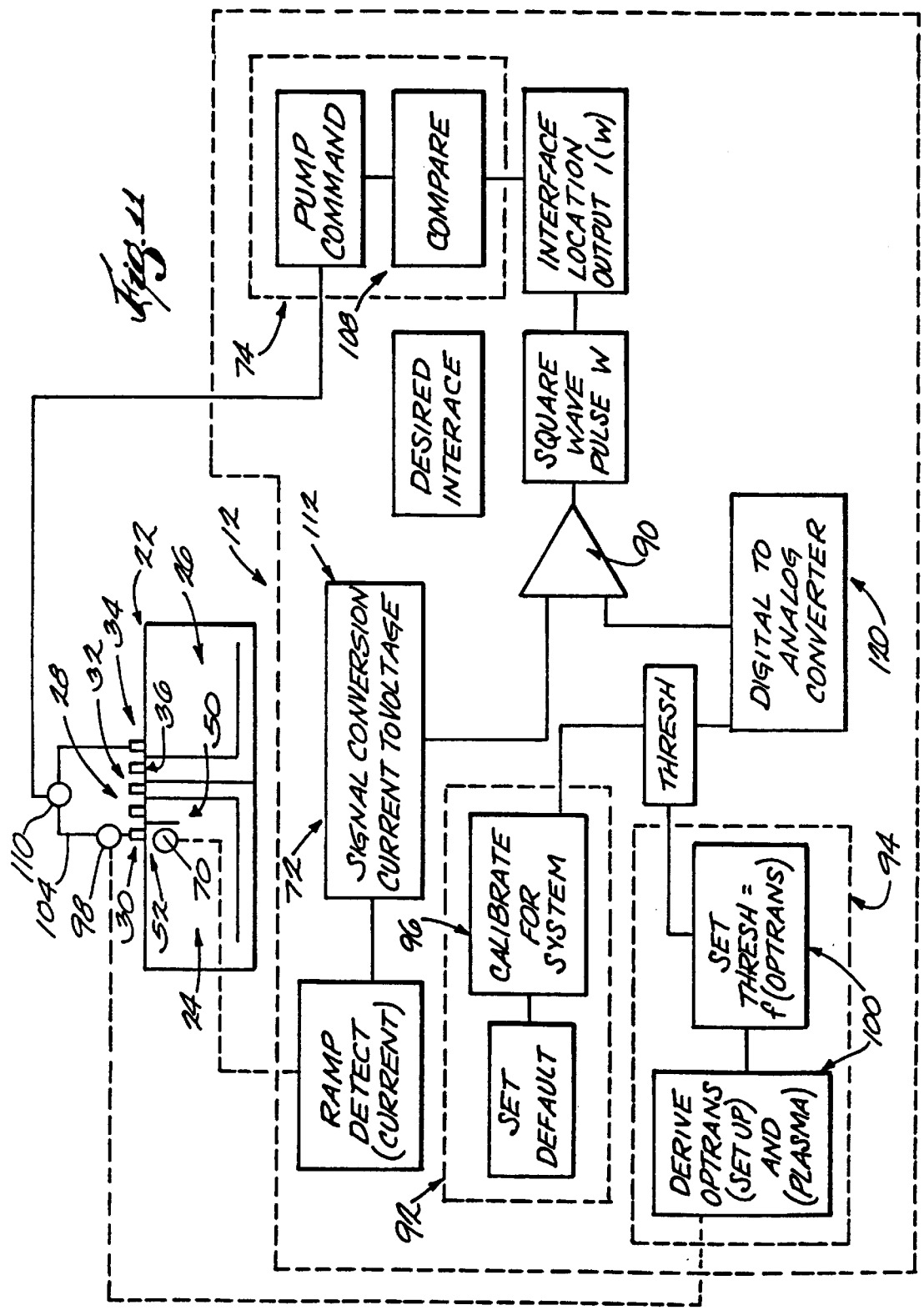
FIG. 11 is a schematic view of the interface processing element and the interface command element, which form a part of the interface controller.

As FIG. 11 shows, the interface processing element 72 includes a signal converting element 112, which converts the sensed light intensity output of the detector 78 (a current) to an amplified voltage signal.

Figure 12:
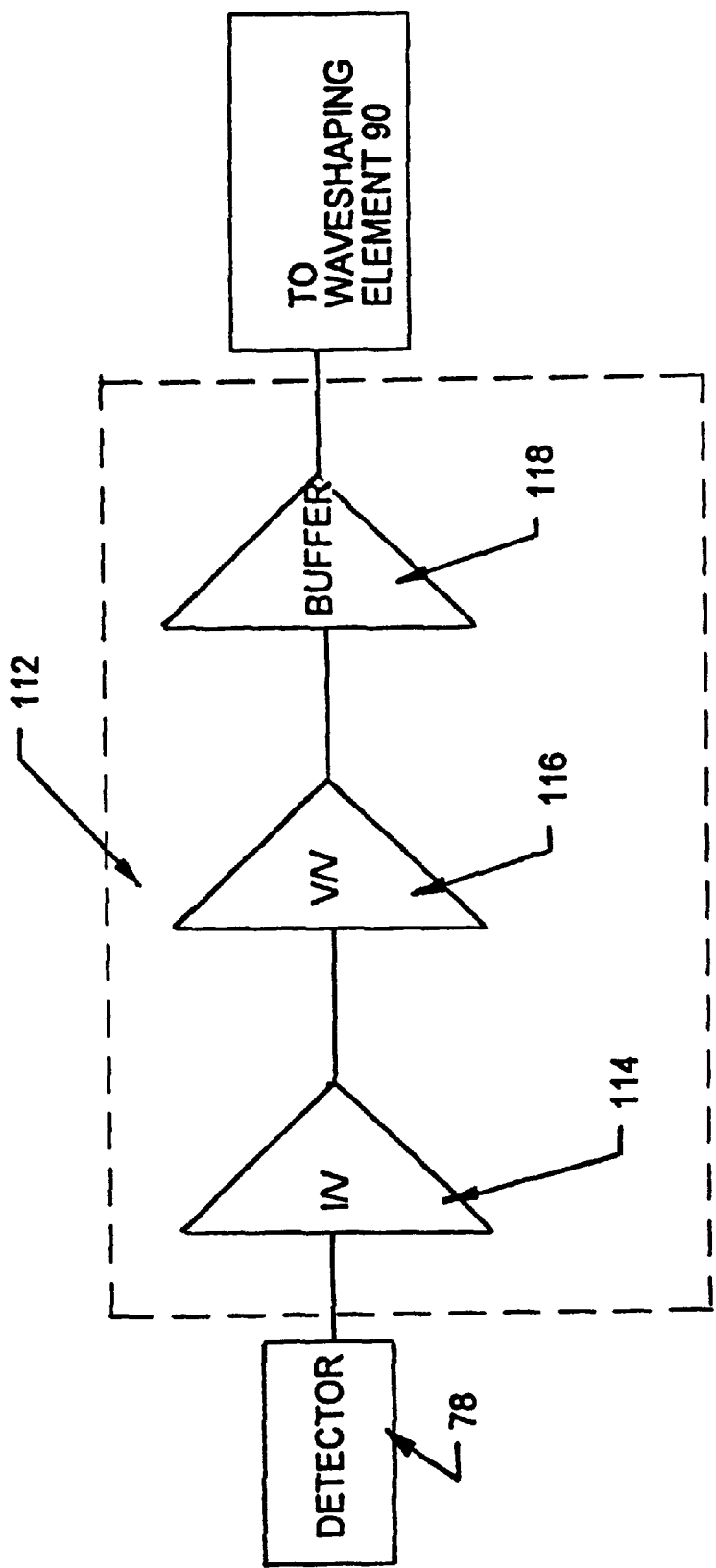
FIG. 12 is a schematic view of the signal converting element, which forms a part of the interface processing element shown in FIG. 11.

As FIG. 12 shows, the signal converting element 112 includes an inverting current to voltage (I/V) amplifier 114, which converts the relatively low positive current signal from the detector 78 (typically, in $\mu A$) to an amplified negative voltage signal. The current-to-voltage gain of the amplifier 114 can vary. In a representative embodiment, the gain is on the order of 58,000, so that current of, for example, 1 $\mu A$ is converted to a voltage signal of −58 mV. A non-inverting voltage amplifier (V/V) 116 further amplifies the negative voltage signal (in mV) to a negative voltage signal (in V) (i.e., a gain of about 400). This twice amplified negative voltage signal is passed through a buffer 118. The output of the buffer 118 constitutes the output of the signal converting element 112. In the illustrated embodiment, the total amplification factor (from detector current signal to processed negative voltage signal) is about 23 million.

Figure 13:
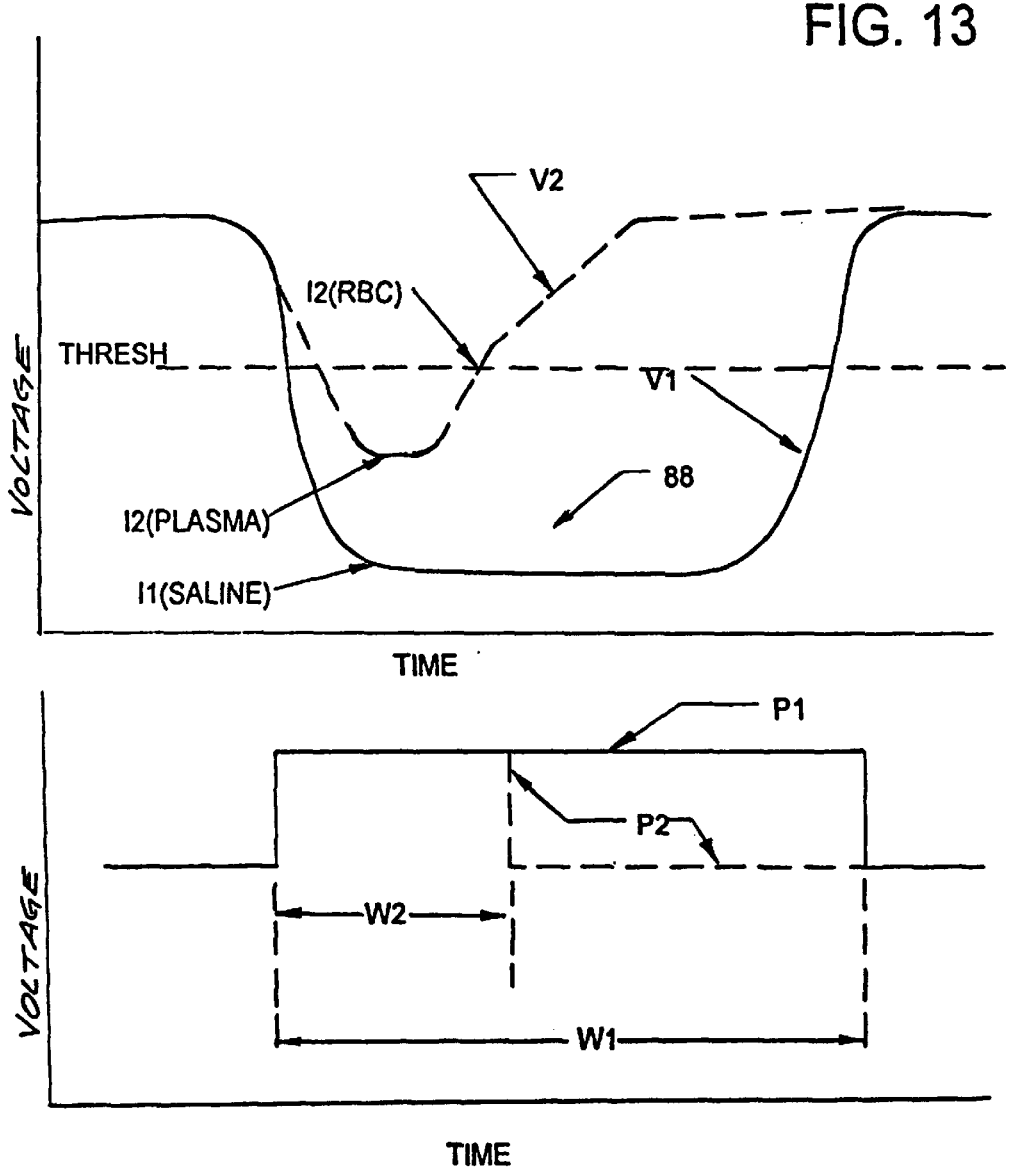
FIG. 13 shows, in its upper portion, a voltage signal generated by the viewing head when passing along the interface ramp and, in its lower portion, a square waveform, which the processing element of the interface controller generates from the voltage signal for the purpose of analyzing the location of the interface on the ramp.

FIG. 13 shows in solid lines a representative curve (designated V1), which plots representative negative voltage outputs of the signal converting element 112 for light signals detected when a light transmissive liquid, e.g., saline, resides along the entire length of the ramp 66. The curve V1 shows the region 88 where the light signal detected increase, level out, and then decrease, as the transparent region 82 and viewing head 70 pass into and out of alignment. In the illustrated embodiment, the voltage curve V1 is negative-going for increasing light signals, due to processing by the signal converting element 112. It should be appreciated that the light signals could be processed to provide a non-inverted voltage output, so that the voltage curve V1 would be positive-going for increasing light signals.

Referring back to FIG. 11, a waveshaping element 90 converts the amplified voltage signals to a square wave time pulse. In the illustrated embodiment, the element 90 comprises a voltage comparator, which receives as input the amplified voltage signals and a selected threshold value (THRESH). The output of the voltage comparator 88 is one (1) when the voltage signal lies below THRESH (that is, when the voltage signal lies further from zero than THRESH) and zero (0) when the voltage signal lies above THRESH (that is, when the voltage signal lies closer to zero than THRESH).

In the illustrated embodiment, THRESH comprises a digital number between 0 and 4095. The digital number is converted by a 12 bit digital-to-analog converter 120 to a voltage analog value between +10 and −10. For example, a digital number of zero (0) for THRESH represents an analog output of +10V, while a digital number of 4095 for THRESH represents an analog output of −10V.

FIG. 13 shows in solid lines a representative square wave pulse (designated P1) processed by the comparator 90 from the voltage curve V1, based upon a selected value for THRESH. Negative-going voltage curve V1 varies from zero (0) (when no light is sensed by the detector 70) to −13.5 V (when maximum light is sensed by the detector 70), and THRESH is the digital number 3481, which the converter 120 converts to an analog voltage value of −7V. The square wave pulse P1 has a width (designated W1 in FIG. 13) expressed in terms of time. The width W1 is proportional to the time that a light signal below THRESH is detected (that is, when the negative voltage signal is farther from zero (0) than analog voltage value of THRESH).

As FIG. 13 shows, maximum light is detected (negative-going voltage signal at −13.5 V) when the interface viewing region 82 and the viewing head 70 align. When a light transmissive material like saline resides along the entire interface ramp 66, the width W1 of the square wave pulse P1 is proportional to the entire time period that the interface viewing region 82 and viewing head 70 align. Width W1 will also be called the baseline pulse width, or BASE.

When material having a high-relative light absorption properties, such as RBC, occupies a portion of the ramp 66, the profile of the sensed voltages changes. FIG. 13 shows in phantom lines a representative curve (designated V2), which plots representative processed voltage signals detected when RBC occupy about 70% of the length of the ramp 66. Negative-going voltage curve V2 varies from zero (0) (when no light is sensed by the detector 70) to −9.9 V (when maximum light is sensed by the detector 70). The curve V2 follows the path of V1 until the detector 78 senses the plasma layer 58, which is not a transmissive to light as saline. The maximum sensed signal intensity for plasma ($I2_{PLASMA}$) (for example, −9.9 V) is therefore less than maximum sensed signal intensity for saline ($I1_{SALINE}$) (for example −13.5 volts). The time period during which $I2_{PLASMA}$ exists is also significantly shorter than the time period which $I1_{SALINE}$ exists. Curve V2 shows the gradual decrease in the sensed voltage signal as the light absorbing RBC layer 56 comes progressively into the field of view of the head 70 (which is generally designated $I2_{RBC}$ in FIG. 13). Curve V2 eventually joins the path of curve V1, as the transparent region 82 and viewing head 70 pass out of alignment.

FIG. 13 also shows in phantom lines that the relative width (W2) of square wave pulse (P2), processed by the comparator 90 using the same THRESH as P1, shortens. The width (W2) diminishes in proportion to the width of the RBC layer 56 relative to the width of the plasma layer 58 on the ramp. As the RBC layer 56 occupies more of the ramp 66, i.e., as the RBC-plasma interface 60 moves closer to the constricted passage 68, the pulse width (W2) shortens relative to the baseline pulse width (W1), and vice versa.

Thus, and by comparing the width of a given pulse wave (such as W2) relative to the baseline pulse width (W1), the interface processing element 72 assesses the relative physical location of the interface 60 on the ramp 66.

As FIG. 11 shows, the interface processing element 72 includes calibration modules 92 and 94 to assure that the optically derived physical location of the interface 66 accurately corresponds with the actual physical location of the interface 66. The first calibration module 92, also called the system calibration module, takes into account the geometry of the spool 18 and ramp 66, as well as operational conditions that can affect the optical acquisition of interface information. The second calibration module 94, also called the blood calibration module, takes into account the physiology of the donor's blood, in terms of the optical density of his or her plasma.

(i) System Calibration Module

The nominal value of the baseline pulse width BASE (expressed in units of time) is selected for a given system. In a representative embodiment, a value of, for example, 640 μsec can be selected for BASE. BASE (in microseconds) is converted to a digital count value (COUNTS), as follows:

$$COUNTS = \left(\frac{BASE}{PERIOD} * SCALE\right) + THRESH_{ZERO} \quad (1)$$

where

SCALE is a selected scale factor (which, in the illustrated embodiment, can be, for example, 80604);

$THRESH_{ZERO}$ is the digital threshold number that represents an analog threshold voltage output of zero (which, in the illustrated embodiment, is 2048); and PERIOD is the period of rotation of the detector 70, based upon the speed of rotation of the detector 70 ($DETECTOR_\Omega$), calculated as follows:

$$PERIOD = \left(\frac{60}{DECTECTOR_\Omega}\right) \times 10^6$$

Once calculated for a given $DETECTOR_\Omega$, COUNTS need not be recalculated at different values of $DETECTOR_\Omega$, provided BASE is not changed.

The system calibration module 92 derives a square pulse wave $P_{SALINE}$, like P1 in FIG. 13, by conveying a light transmissive liquid, such as saline, through the chamber 22, while sampling voltage values along the ramp 66. The voltage value samples are processed by the comparator 90 to create the square wave pulse $P_{SALINE}$, using an estimated initial threshold value $THRESH_{START}$. The width $W_{START}$ of the pulse $P_{SALINE}$ formed using $THRESH_{START}$ is measured and compared to the baseline width BASE, which is determined according to Equation (1).

Moving THRESH closer to zero than $THRESH_{START}$ will increase the pulse width, and vice versa. When $W_{START}$ does not equal BASE, or, alternatively, if $W_{START}$ falls outside a specified satisfactory range of values for BASE, the system calibration module 92 varies the threshold value from $THRESH_{START}$ to vary the pulse width, until the pulse width of $P_{SALINE}$ meets the target criteria for BASE. The threshold value that achieves the target baseline pulse width BASE becomes the default threshold value $THRESH_{DEFAULT}$ for the system.

Despite the derivation of $THRESH_{DEFAULT}$, variations in sensed pulse width can occur during normal use independent of changes in the actual physical dimension of the interface. For example, sensed voltage signals can change due to changes occurring within the viewing head 70, such as loss of focus, deposition of foreign materials on optical surfaces, shifts in optical alignment, or weakening of the light emitting diodes 80 or detector 78. Sensed voltage signals will change due to degradation of optical performance, independent of and unrelated to changes in the physical dimensions of the interface. When processed by the converter 90 using $THRESH_{DEFAULT}$, the changed voltage signals can result in a reduced or enlarged pulse width, which may no longer accurately reflect the actual state of the interface. Erroneous control signals may result.

In the illustrated and preferred embodiment, the system calibration module 92 includes a set up protocol 96. The protocol 96 sets a threshold value THRESH to obtain the baseline pulse width BASE using actual performance conditions existing at the beginning of each processing cycle.

The set up protocol 96 commands the system to convey saline (or other selected light transmissive material) through the separation chamber 22, as before described in connection with deriving $THRESH_{DEFAULT}$. A representative number of samples (e.g., 10 samples) of pulse widths $W_{DEFAULT(1\ to\ n)}$ are obtained based upon sensed voltage values using $THRESH_{DEFAULT}$. The sample pulse widths are averaged $W_{DEFAULT(AVG)}$ and compared to BASE for the system, derived according to Equation (1). If $W_{DEFAULT(AVG)}$ equals BASE, or, alternatively, lies within an acceptable range of values for BASE, THRESH is set at $THRESH_{DEFAULT}$.

In a representative implementation, the protocol 96 uses the following criteria is used to evaluate $THRESH_{DEFAULT}$:

IF $W_{DEFAULT(AVG)} \geq BASE_{LOWER}$

AND $W_{DEFAULT(AVG)} \leq BASE_{UPPER}$

THEN $THRESH = THRESH_{DEFAULT}$ where:

$BASE_{UPPER}$ is a selected maximum value for the baseline pulse width, e.g., BASE times a selected multiplier greater than 1.0, for example 1.0025; and $BASE_{LOWER}$ is a selected minimum value for the baseline pulse width, e.g., BASE times a selected multiplier less than 1.0, for example 0.9975.

If the $W_{DEFAULT(AVG)}$ does not meet the above criteria, the set up procedure searches for a value for THRESH that brings $W_{DEFAULT(AVG)}$ into compliance with the established criteria for BASE. Various search algorithms can be used for this purpose.

For example, the set up procedure can use a half-step search algorithm, as follows:

where THRESH is the name given to the interface threshold value selected; $THRESH_{UPPER}$ is a set maximum value for THRESH; $THRESH_{LOWER}$ is a set minimum value for THRESH; and $W_{SAMPLE\ (AVG)}$ is an average of pulse widths taken during a set sample period.

set $THRESH_{n-1} = THRESH_{DEFAULT}$ set $THRESH_{UPPER}$ set $THRESH_{LOWER}$

DO n = 2 to 20

IF $W_{SAMPLE(AVG)} > BASE_{UPPER}$ THEN $THRESH_{LOWER} = THRESH_{n-1}$ $THRESH_n = (THRESH_{LOWER} + THRESH_{UPPER})/2$

-continued

ELSEIF $W_{SAMPLE(AVG)} < BASE_{LOWER}$

THEN $THRESH_{UPPER} = THRESH_{n-1}$ $THRESH_n = (THRESH_{UPPER} + THRESH_{LOWER})/2$

ELSIF end the search

ENDIF

END DO

IF n = 20 THEN

Activate a Warning Alarm:

Interface Detector Problem

ENDIF

The system calibration module 92 thereby assures that the optically derived location of the interface 66 is not skewed based upon operational conditions that can affect the optical acquisition of interface information.

(ii) Blood Calibration Module

The interface controller 12 can operate on the premise the optical density of the donor's plasma residing on the ramp 66 is substantially equivalent to the optical density of the material (e.g., saline) used by the system calibration module 92 at the outset of a given procedure. Typically, the optical density of normal plasma can be considered equivalent to saline.

However, the optical density of plasma will vary according to the concentration of platelets carried in the plasma. Therefore, plasma particularly rich in platelets, which is a processing goal of the system 10, has a density that differs significantly from saline or normal plasma.

The optical density of plasma will also vary according to the concentration of lipids in the plasma, which depends upon the physiology or morphology of the individual donor. Lipemic plasma has a density that differs significantly from saline or non-lipemic plasma.

The presence of plasma on the ramp 66 carrying high concentrations of platelets or lipids, diminishes the magnitude of the sensed voltage signals, independent of and unrelated to changes in the physical dimensions of the interface. When processed by the converter 90 using THRESH, set by the system calibration module 92 just described, the associated square wave pulses possess a reduced pulse width. The reduced pulse width is caused by the physiology of the donor's blood, and does not accurately reflect the actual state of the interface.

For example, a RBC-plasma interface 60 located at the proper position on the ramp 66 will, in the presence of lipemic plasma or very platelet rich plasma, generate a pulse width, which is otherwise indicative for normal plasma of an RBC-plasma interface 60 that is too close. The artificially reduced pulse width will generate an error signal, which commands a reduction in the rate at which plasma is conveyed through the port 34. The previously properly positioned interface 60 is needlessly shifted to an out-of-position location down the ramp 66.

Figure 14:
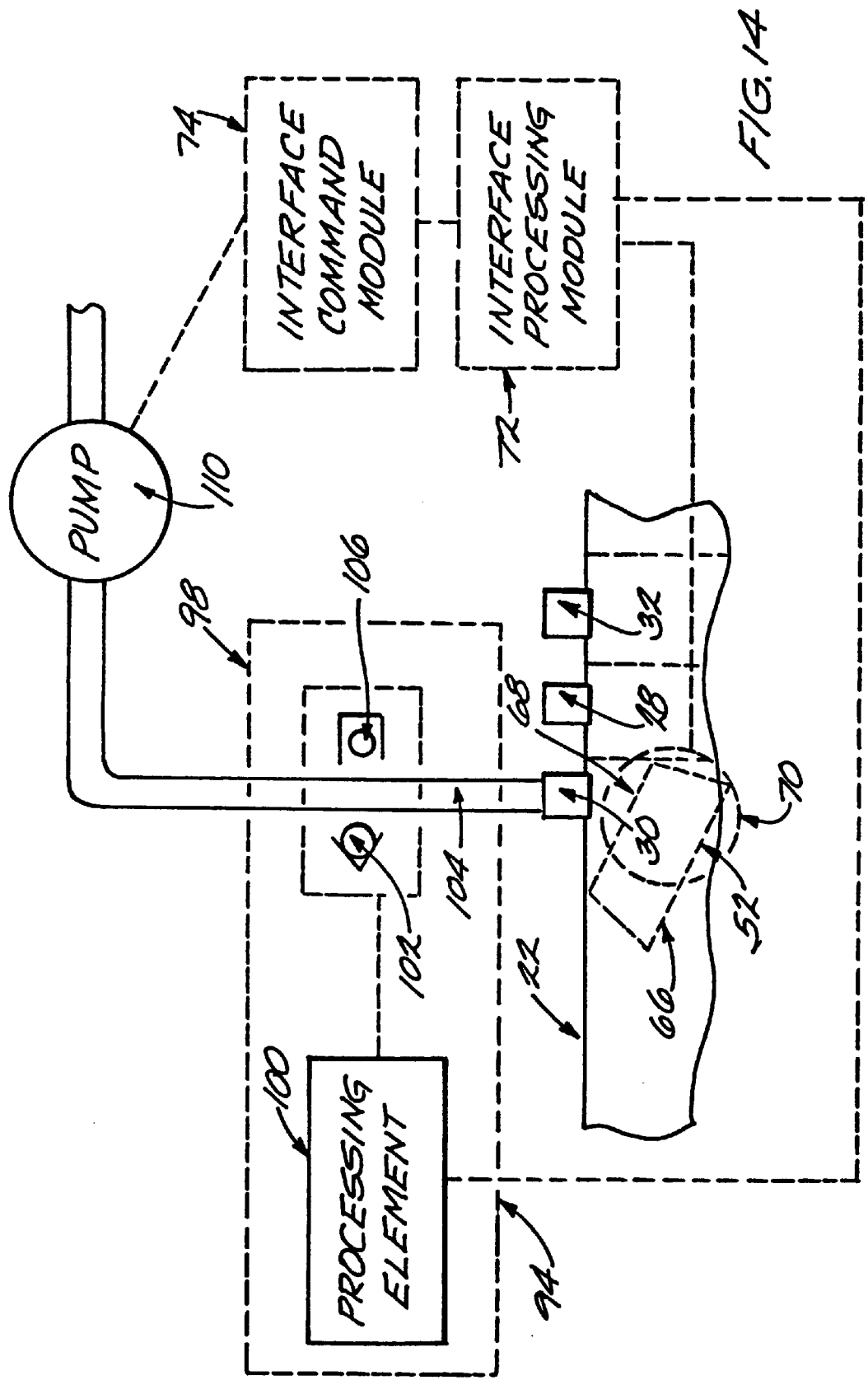
FIG. 14 is a schematic view of the blood calibration element, which forms a part of the interface controller.

The second calibration module 94 adjusts the pulse width in the presence of plasma having an optical density significantly different than saline, to reflect the true position of the interface and thereby avoid blood-related optical distortions. The module 94 includes an optical monitor 98 (see FIG. 14), which senses the optical density of plasma exiting the plasma outlet port 30 or entering the PRP inlet port 34. In the illustrated embodiment shown in FIG. 13, the optical monitor 98 is a conventional hemoglobin detector, used on the Autopheresis-C® blood processing device sold by the Fenwal Division of Baxter Healthcare Corporation. The monitor 98 comprises a red light emitting diode 102, which emits light into the plasma outlet tubing 104. In this arrangement, the wavelength for detecting the optical density of plasma is essentially the same as the wavelength for detecting the location of the interface. Of course, other wavelengths, like green or infrared, could be used. The monitor 98 also includes a PIN diode detector 106 on the opposite side of the tubing 104.

Using the essentially the same wavelength for monitoring the interface and monitoring plasma is a preferred implementation. Using essentially the same wavelengths makes the absorbance spectrum for plasma essentially the same for both detectors. Therefore, there is no need to correlate the absorbance spectrum of the interface detector to the absorbance spectrum of the plasma detector. Of course, different wavelengths can be used, if desired, in which case the absorbance spectrums for plasma of the different wavelengths should be correlated, to achieve accurate calibration results.

The second calibration module 94 also includes a processing element 100, which receives signals from the monitor 98 to compute the optical transmission of the liquid conveyed through the tubing 104, which is called OPTTRANS. Various algorithms can be used by the processing element 100 to compute OPTTRANS. In a representative embodiment, OPTTRANS is derived, as follows:

$$OPTTRANS = \frac{COR(RED\ SPILL)}{CORREF} \quad (2)$$

where COR(RED SPILL) is calculated as follows:

COR(RED SPILL)=RED−REDBKGRD where:
RED is the output of the diode detector when the red light emitting diode is on and the liquid flows through the tubing;
REDBKGRD is the output of the diode detector when the red light emitting diode is off and the liquid flows through the tubing;

and where CORREF is calculated as follows:

CORREF=REF−REFBKGRD where:
REF is the output of the red light emitting diode when the diode is on; and
REFBKGRD is the output of the red light emitting diode when the diode is off.

Operating with the system calibration module 92, the processing element 100 obtains data from the monitor 98 and derives the optical transmission of the tubing and the light transmissive, set up liquid, such as saline. In a preferred embodiment, optical transmission values are calculated at the fastest possible rate during the set up procedure. The values are averaged over the entire set up procedure to derive an optical transmission value for the tubing and setup liquid ($OPTTRANS_{SETUP}$).

After set up is complete, and the system calibration module 92 is no longer operative, the blood calibration module 92 continues during subsequent blood processing to derive the optical transmission of the tubing and plasma using Equation (2). In the preferred embodiment, optical transmission values are calculated by the processing element 100 at the fastest possible rate during the blood processing procedure. The values are periodically averaged at the end of a set sampling interval (for example, every 180 seconds) to derive an optical transmission value for the tubing and plasma (OPTTRANS$_{PLASMA}$).

At the end of each set sampling interval (i.e., every 180 seconds, for example), the processing module 100 determines a new threshold value THRESH, for deriving the pulse width, which varies as a function of OPTRANS, as follows:

$$THRESH = THRESH_n - \left[\frac{1 - OPTRANS_{PLASMA}}{OPTRANS_{SETUP}}\right] * MULT \quad (3)$$

where MULT is a predetermined scale factor from 0 to, for example, 1000. In the illustrated embodiment, MULT can be set at 200.

The foregoing correction of THRESH increases the pulse width in relation to increases in optical density of plasma on the ramp 66. The second calibration module 94 thereby takes into account diminution in voltage signal gain in the presence on the ramp 66 of lipemic plasma or plasma with very high platelet counts. The second calibration module 94 thereby serves as a gain controller for the interface controller 12, adjusting the width of the pulse to accurately reflect the actual physical location of the interface on the ramp, despite the presence of plasma having greater than normal optical density.

The interface processing element 72 ultimately outputs a signal, which accurately represents the interface location as a function of W. For example, when BASE=640 $\mu$sec, a measured pulse width W indicates that 100% of the ramp 66 is occupied by plasma. A measured pulse width W of 320 $\mu$sec indicates that plasma occupies 50% of the ramp 66, while a measured pulse width W of 192 $\mu$sec indicates that plasma occupies 30% of the ramp 66 (i.e., RBC occupy 70% of the ramp 66), and so on.

The foregoing description shows the processing element 72 receiving sensed light intensity values from an interface detector 70 that senses light reflected from the interface ramp 66. It should be appreciated that comparable light intensity values can be obtained for processing by the processing element 72 from an interface detector that senses light after transmission through the interface ramp 66, without back reflection. In this alternative embodiment, a light source is carried by the yoke 20 (in the same manner as the optical head 70), and a light detector is carried by the spool 18 behind the interface ramp 66, or vice versa.

(3) Interface Command Element

As FIG. 11 shows, the interface command element 74 receives as input the interface location output of the processing element 72. The command element includes a comparator 108, which compares the interface location output with a desired interface location to generate an error signal (E). The desired interface location is expressed as a control value consistent with the expression of the interface dimension output.

Generally speaking, for platelet collection, RBC should occupy no more than about 60% to 65% of the ramp 66. This can conversely be expressed in terms of a control value (expressed as a percentage) of between 35% to 40% of BASE, meaning that the measured pulse width W should be 35% to 40% of its maximum value. Alternatively, the control value can be expressed in terms of a number representing a pulse width value (in time units) integrated to a voltage value proportional to the percentage of plasma occupying the ramp 66.

Of course, different control values can be used depending upon the particular blood component collection objectives.

When the control value is expressed in terms of a targeted RBC percentage value, a positive error signal (+E) indicates that the RBC layer 56 on the ramp 66 is too large (as FIG. 6 shows). The interface command element 74 generates a signal to reduce the rate which PRP is removed through port 34. The interface 60 moves away from the constricted passage 68 toward the desired control position (as FIG. 5 shows), where the error signal (E) is zero.

A negative error signal (−E) indicates that the RBC layer 56 on the ramp 66 is too small (as FIG. 7 shows). The interface command element 74 generates a signal to increase the rate at which PRP is removed through the port 34. The interface 60 moves toward the constricted passage 68 toward the desired control position (FIG. 5), where the error signal (E) is again zero.

The interface command element 74 can affect the rate at which plasma is removed through the port 34 by controlling the relative flow rates of WB, the RBC, and the PRP through their respective ports. In a preferred embodiment (as FIGS. 11 and 13 show), a pump 110 draws PRP via the tubing 104 through the port 34. The command element 74 controls the pump rate of the pump 110 to keep the interface 60 at the prescribed location on the ramp 66, away from the constricted passage 68.

D. Optical Derivation of Platelet Volumes

Figure 15:
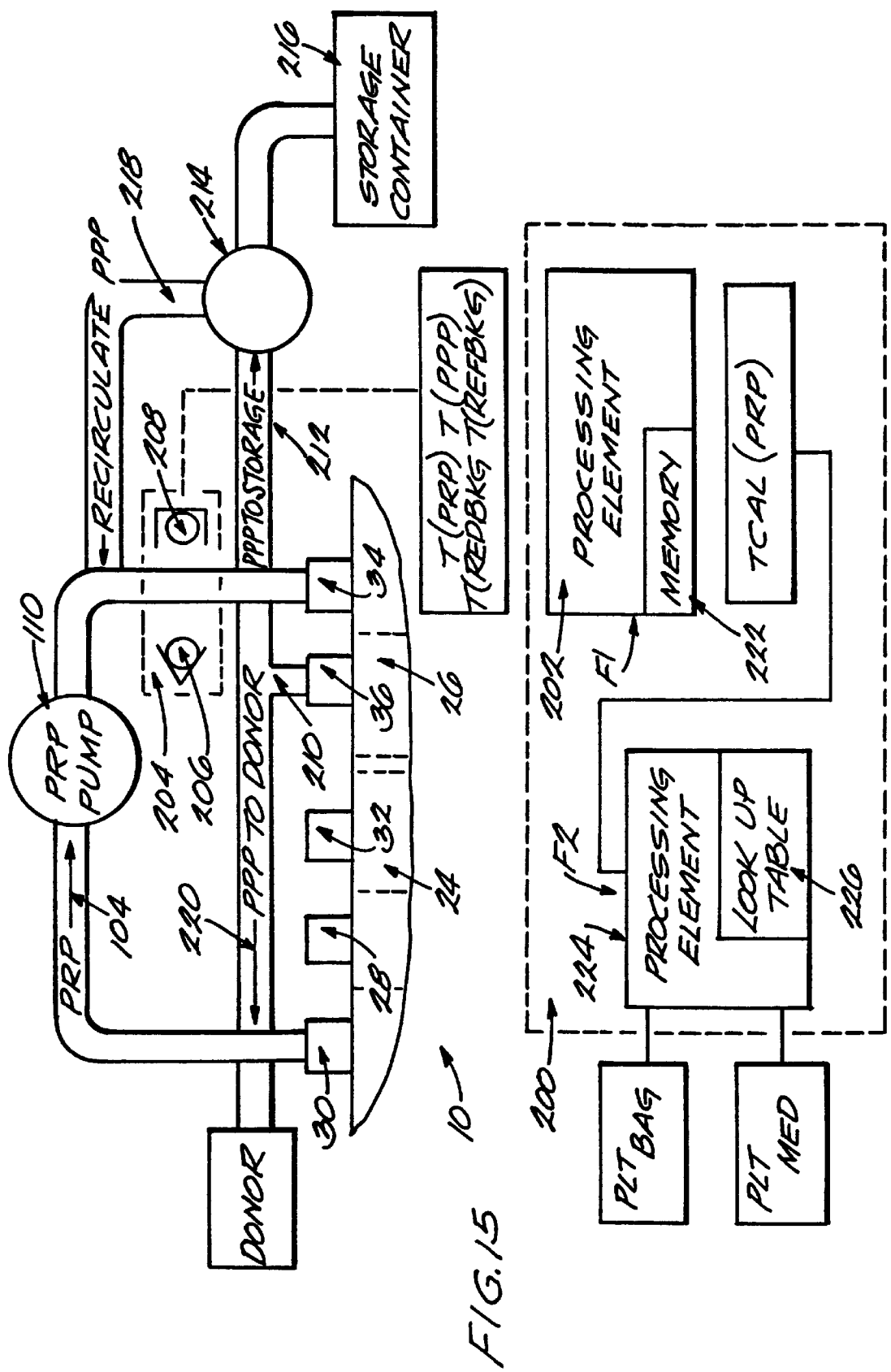
FIG. 15 is a schematic view of the first and second utility functions of the processing control application, which forms a part of the blood processing system shown in FIG. 1, as well as the associated monitor which optically monitors the opacity of PRP transported from the separation chamber.

As FIG. 15 shows, the system 10 preferably also includes a processing control application 200, which comprises one or more utility functions, two of which, F1 and F2, are shown. The one or more utility functions F1 and F2 provide processing status and parameter information and generate processing control variables for the system 10. The one or more utility functions F1 and F2 are designed to achieve specified blood processing goals, taking into account the individual morphology of the donor and actual conditions occurring as processing proceeds.

The number and type of utility functions can vary. For example, a particular utility function can derive the yield of platelets during a given processing session, estimate the processing time before commencing a given processing session and while the processing session is underway, or generate control variables that control the rate of citrate anticoagulant infusion during a given processing session. Examples of utility functions are detailed in Brown U.S. Pat. No. 5,639,382, entitled "Systems and Methods for Deriving Recommended Storage Parameters For Collected Blood Components" which is incorporated herein by reference.

In the illustrated embodiment, the processing control application 200 includes at least first and second utility functions F1 and F2. The first utility function F1 generates an optically derived processing value, based upon on line monitoring of the opacity of the donor's platelet-rich plasma (PRP) during processing. The optically derived processing value correlates with the volume of platelets collected, and thereby obviates the need to calculate the platelet collection volume based upon off line cell counting and sizing techniques. The correlation between the optically derived processing value and the volume of platelets collected also obviates the need for a calibration factor to bring data derived on line into conformance with date derived off line.

The second utility function F2 calculates optimal storage parameters for the platelets collected, based upon the processing value optically derived by the first utility function F1. The second utility function F2 specifies these parameters in terms of the number of storage containers and the volume of platelet-poor plasma (PPP) to use as a platelet storage medium.

(1) The Utility Function F1

The utility function F1 employs a processing element 202 coupled to an optical monitor 204, which is positioned to sense the overall optical transmission of PRP separated from whole blood in the first stage 24 of the chamber 22. This overall optical transmission value for PRP will be called T(PRP).

The processing element 202 calibrates the overall value T(PRP) against a baseline value, which will be called T (PPP). The baseline value T(PPP) reflects the optical transmission of the donor's plasma in the absence of platelets, which also takes into account the lipid content of the donor's plasma. The processing element 202 also preferably calibrates T(PRP) and T(PPP) against optical background "noise."

Ultimately, the processing element 202 derives a calibrated opacity value, called TCAL(PRP), which reflects the opacity of the PRP due solely to the presence of platelets.

The processing element 202 numerically integrates the calibrated opacity value TCAL (PRP) relative to the plasma volume processed over time, to obtain an integrated value called ΣTCAL(PRP). It has been discovered that the magnitude of ΣTCAL(PRP) for a given procedure and donor, using a particular processing system, closely correlates to the platelet yield actually obtained during that procedure (expressed in units×$10^{11}$) and the volume of platelets actually collected during the procedure (expressed in ml). As a result, neither of these actual values need be independently calculated by other means.

(i) The Optical Monitor

In the illustrated embodiment (see FIG. 15), the optical monitor 204 is positioned along tubing 104 to sense the optical density of plasma exiting the plasma outlet port 30 of the first stage 24 or entering the PRP inlet port 24 of the second stage 26. In the illustrated embodiment, the monitor 204 is located in line with the tubing 104 downstream of the PRP pump 110, previously described. Alternatively, the monitor 204 could be placed upstream of the PRP pump 110.

The optical monitor 204 can be constructed in various ways. In the illustrated embodiment shown in FIG. 15, the monitor 204 comprises a conventional hemoglobin detector, used, e.g., on the Autopheresis-C® blood processing device sold by the Fenwal Division of Baxter Healthcare Corporation. The monitor 204 comprises a red light emitting diode 206, which emits light into the plasma outlet tubing 104. Other wavelengths, like green or infrared, could be used.

The monitor 204 also includes a PIN diode detector 208 on the opposite side of the tubing 104.

The wavelength for detecting the optical density of plasma can be essentially the same as the wavelength for detecting the location of the interface, as previously described. In this way, the optical monitor 204 serving the processing element 202 and the optical monitor 98 serving the processing element 100 (previously described and shown in FIGS. 11 and 14) can comprise the same functional element.

(ii) Deriving TCAL (PRP)

As liquid is conveyed through the tubing 104 from the first stage 24 to the second stage 26, the processing element 202 receives signals from the monitor 204, indicative of the optical transmission of the liquid in the tubing 104. When the liquid is PRP, the signals are indicative of T(PRP), which varies as a function of the number and size of platelets residing in the PRP. The T(PRP) signals also vary as a function of the lipid content of the donor's plasma, in the manner previously described, as well as any background optical "noise" unrelated to the opacity of the PPP or PRP. The processing element 202 takes these factors affecting the opacity signals into account to compute a calibrated value TCAL (PRP), which varies solely as a function of the density of platelets residing in the PRP.

Various algorithms can be used by the processing element to compute TCAL(PRP).

In a preferred embodiment, T(PRP) is adjusted to obtain TCAL(PRP), as follows:

$$TCAL(PRP) = \frac{T(PRP) - T(REDBKG)}{T(PPP) - T(REFBKG)} \qquad (4)$$

where:
T(PRP) represents the output of the diode detector 208 when the red light emitting diode 206 is on and PRP flows through the tubing 104;
T(REDBKD) is the output of the diode detector 208 when the red light emitting diode 206 is off and PRP flows through the tubing 104;
T(PPP) is the output of the diode detector 208 when the diode 206 is on and PPP or its equivalent flow through the tubing; and
T(REFBKG) is the output of the diode detector 208 when the diode 206 is off and no liquid flow through the tubing 104.

The values T(PRP), T(PPP), T(REDBKG), and T(REFBKG) each comprises a digital number between 0 (maximum light transmission) to 2048 (no light transmission). The digital number is obtained by converting the sensed light intensity output of the detector 208 (a current) into a negative voltage signal using an inverting current to voltage (I/V) amplifier. The negative voltage signal is further amplified, buffered, and processed in a conventional manner to provide the digital number output.

In the illustrated and preferred embodiment, the values T(PRP), T(PPP), T(REDBKG), and T(REFBKG) are obtained by straight through transmission between a single emitter 206 and a single detector 208 and include no side scatter effects.

(iii) Deriving Baseline T(PPP)

In the illustrated embodiment (see FIG. 15), platelet-poor plasma (PPP) is centrifugally separated from PRP in the second stage 26. During processing, PPP is conveyed from the second stage 26 through the port 36, leaving PC in the second stage 26.

Tubing 210 communicates with the PPP port 36. The tubing 210 includes a first branch 212, which leads (via an in line pump 214) to a collection container 216. During the platelet collection stage of processing, a designated volume of the PPP is retained in the container 216 for eventual use as a suspension medium for the PC. Following the platelet-collection stage of the process, a suspension stage is begun, during which all or a portion of the PPP in the container 216 is conveyed back into the second stage 26, via tubing branch 218, to suspend the PC for storage and transfusion.

The tubing 210 also includes a second branch 220, which leads to the donor. The second branch 220 conveys the remaining volume of PPP (i.e., the portion not designated for use as a suspension medium) for return to the donor during processing.

For a system configured as shown in FIG. 15, the platelet-poor plasma baseline T(PPP) can be derived for the individual donor in various ways.

For example:

(i) The value of T(REFBKG) can be obtained at the beginning of the processing period and stored in memory 222 in the processing element 202. The value of T(REDBKD) can be obtained and stored in the same manner at the beginning of the processing period, or values of T(REDBKD) can be sensed periodically during processing (e.g., every 5 seconds) and stored in memory 222. Values of T(PRP) can also be taken at designated sample intervals (e.g., every 5 seconds) during the platelet collection stage and also stored as such in memory 222. The value of T(PPP) can be ascertained during the suspension stage by conveying PPP from the container into the second stage 26 via the tubing 218, thereby passing through the optical monitor 204. The value of T(PPP) obtained during the platelet collection stage can also be stored in memory 222. The processing element 202 can then calculate the values of TCAL (PRP) for each sample interval at the end of the processing period based upon values stored in memory 222. Alternatively, the data retaining in memory 222 can be downloaded for processing in the same manner in an external processing unit.

(ii) Alternatively, the value of T(PPP) can be obtained during the platelet collection stage by periodically circulating a known volume of PPP from the second stage 26 via the pump 214, through the tubing 218, and into tubing 104 upstream of the optical monitor 204. By ascertaining the differential between the T(PRP) value before and after the circulation of PPP volume, and knowing the volume of PPP circulated, the processing element 202 can derive an offset to adjust T(PRP) values obtained during subsequent sample intervals in the platelet collection stage, to thereby obtain TCAL(PRP).

Figure 16:
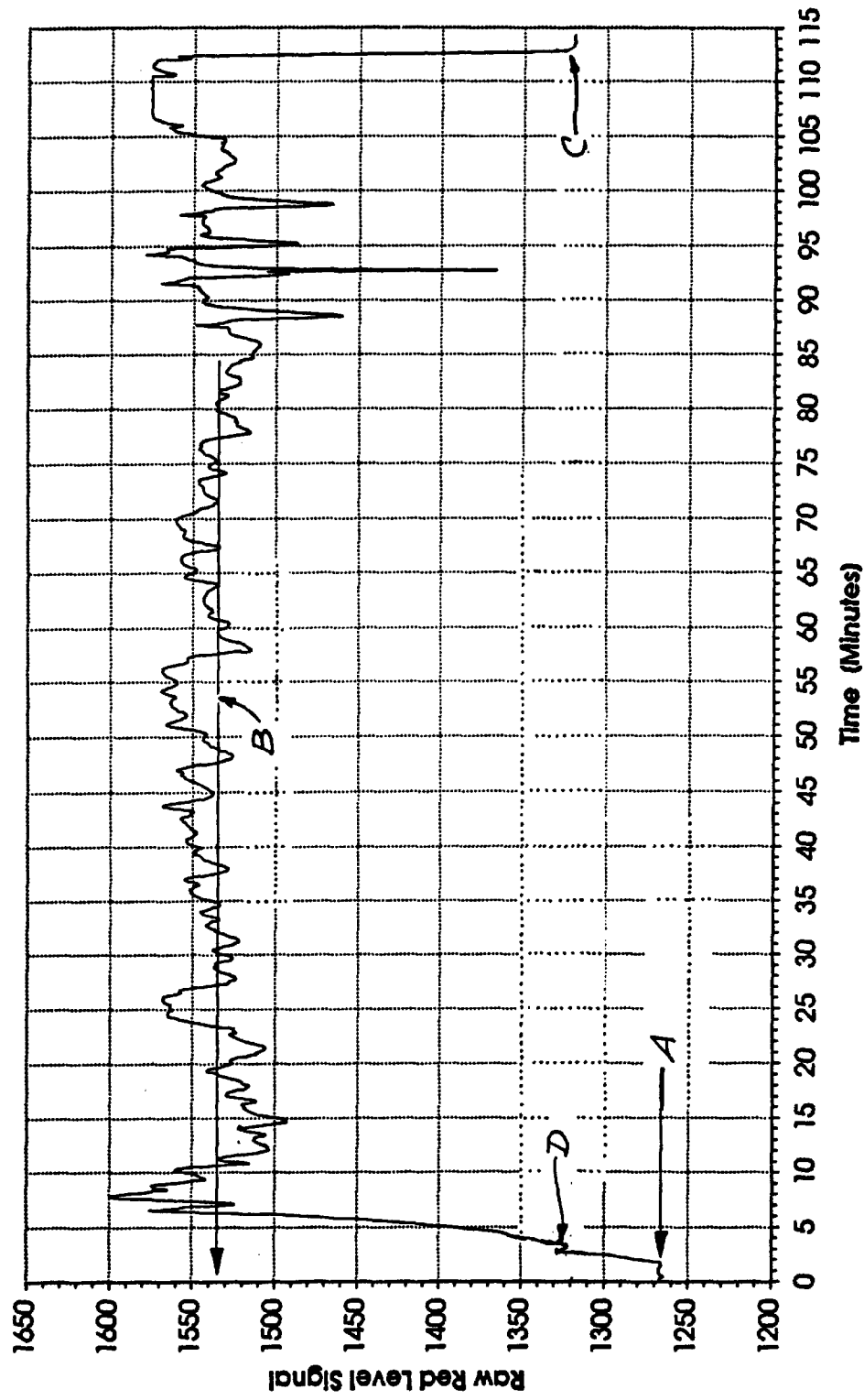
FIG. 16 is a plot showing the fluctuations in the opacity of fluid monitored by the optical monitor shown in FIG. 15, which constitutes an input to the first utility function also shown schematically in FIG. 15.

(iii) Alternatively, the value of T(PPP) can be obtained empirically by plotting the fluctuation of T(PRP) over time during a series of processing periods using a given system, and by ascertaining when the value of T(PRP) obtained during the platelet collection stage matches the value of T(PPP) obtained during the suspension stage. FIG. 16 shows a representative plot of the fluctuation of T(PRP) over time during a typical platelet collection stage and suspension stage, using a centrifugal blood collection system of the type previously described and illustrated. In FIG. 16, T(PRP) is expressed as a raw digital number signal from the diode detector 206, so that the digital number increases with sensed opacity (as before described, between 0 and 2048). The value A represents T(SAL) obtained during a set up stage, as described earlier. The opacity is seen to rise as the platelet collection stage progresses, until a desired constituency of PRP is obtained, under the control of the interface controller 12, as previously described. The value B represents a running average of T(PRP) obtained during the platelet collection stage. The value C represents T(PPP) obtained during the suspension stage. FIG. 16 shows that a corresponding value D, essentially equal to T(PPP) is sensed during the early stages (of the platelet collection stage (e.g., after about 3 minutes, as saline is progressively replaced by PRP). Empirical results demonstrate that, for a given procedure on a given system, the value D, corresponding to T(PPP), consistently occurs after the conveyance of a certain volume of PRP from the first stage 24 during the platelet collecting stage (which in FIG. 16, is about 58 ml). Based upon such empirical data, T(PPP) can be obtained by measuring T(PRP) at a designated point in the platelet collection procedure and assigning T(PPP) its value.

(iv) Deriving ΣTCAL(PRP)

The processing element 202 numerically integrates the values of TCAL(PRP) during the processing period relative to the plasma volume $V_p$ processed. There are various ways in which this numeric integration can be accomplished.

In a preferred implementation, the processing element 202 computes an opacity value T for each sample interval (n), as follows:

$$T_{(n)}=(1-TCAL(PRP)_{(n)})dV_{p(n)} \quad (6)$$

where:

$dv_{p(n)}$ is the incremental plasma volume (in ml) processed during the sample interval(n), which can also be expressed as follows:

$$dV_{p(n)}=Q_{p(n)}\Delta t_{(n)}$$

where:

$Q_{p(n)}$ represents the flow rate of plasma (in ml) through the tubing 104 during the sample interval (n) (which is controlled by the pump 110), and $\Delta t_{(n)}$ is the length of the sample interval (in seconds).

The processing element continuously sums $T_{(n)}$ over the period n=1 to n=END, where END is the length of the processing period (in seconds) divided by $\Delta t$, to obtain ΣTCAL(PRP).

Figure 17:
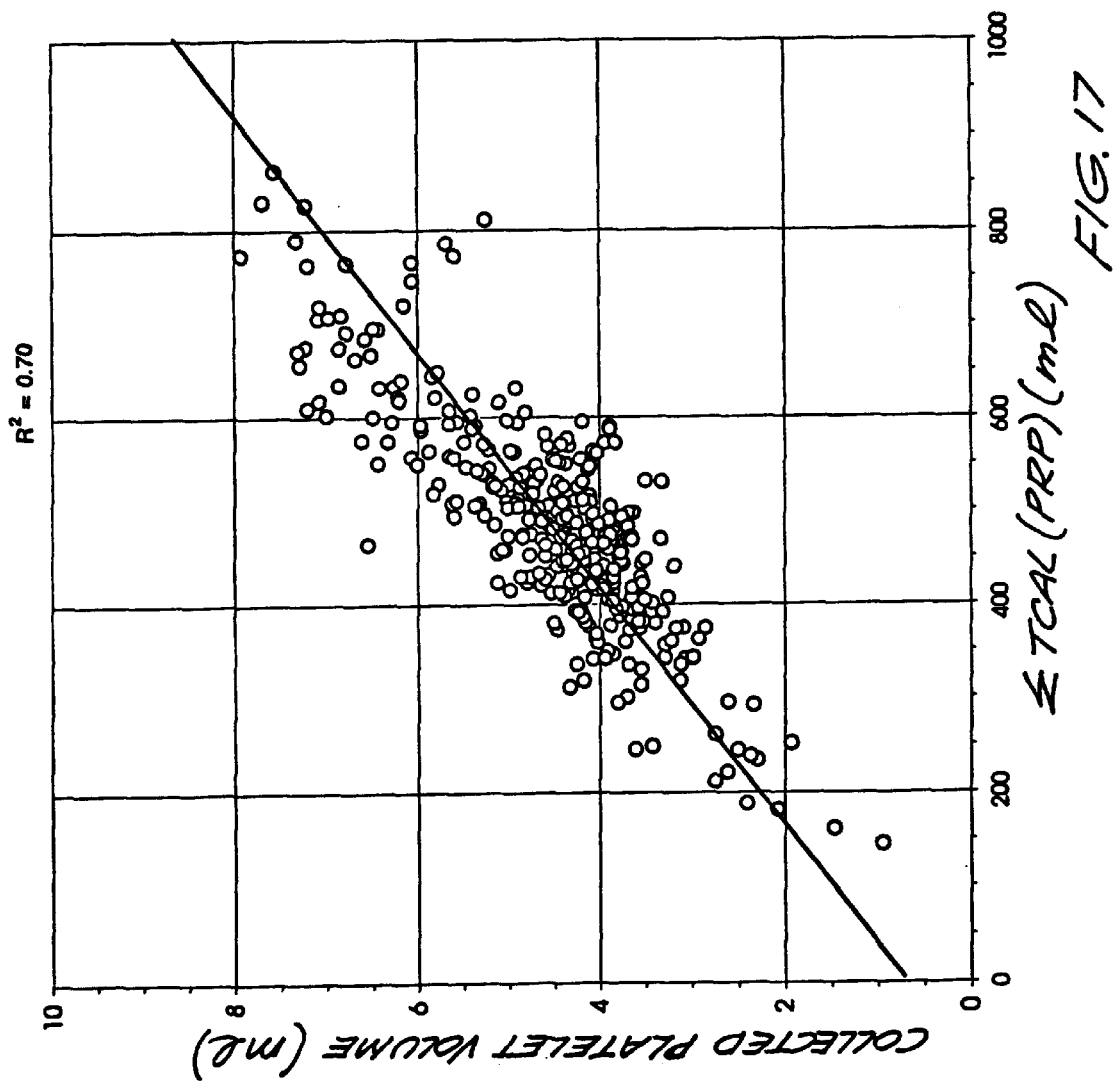
FIG. 17 is a plot showing the correlation of the integrated optical density value derived by the first utility function, shown in FIG. 15, to collected platelet volume data.

FIG. 17 shows a plot of 358 values of ΣTCAL(PRP) derived during blood separation processes of the type previously described, performed by fifteen different centrifuges of the type previously described. The values of ΣTCAL (PRP) are plotted against associated platelet volumes collected (in ml), which are derived by multiplying the number of platelets collected by their mean platelet volume (MPV), as measured by an off line counter. The plot shows a linear distribution having the following relationship:

$$PLT_{Vol}(ml)=0.24+0.0070 \Sigma TCAL(PRP)$$

where 0.24 is the y-intercept, which is only about 6% of the nominal expected collected platelet volume of $4.0 \times 10^{11}$ ml, and 0.0070 is the slope of the plot. The linear distribution has an $r^2$ value of 0.75. FIG. 17 demonstrates that a good correlation exists between ΣTCAL(PRP) and collected platelet volume $PLT_{Vol}$.

Figure 18:
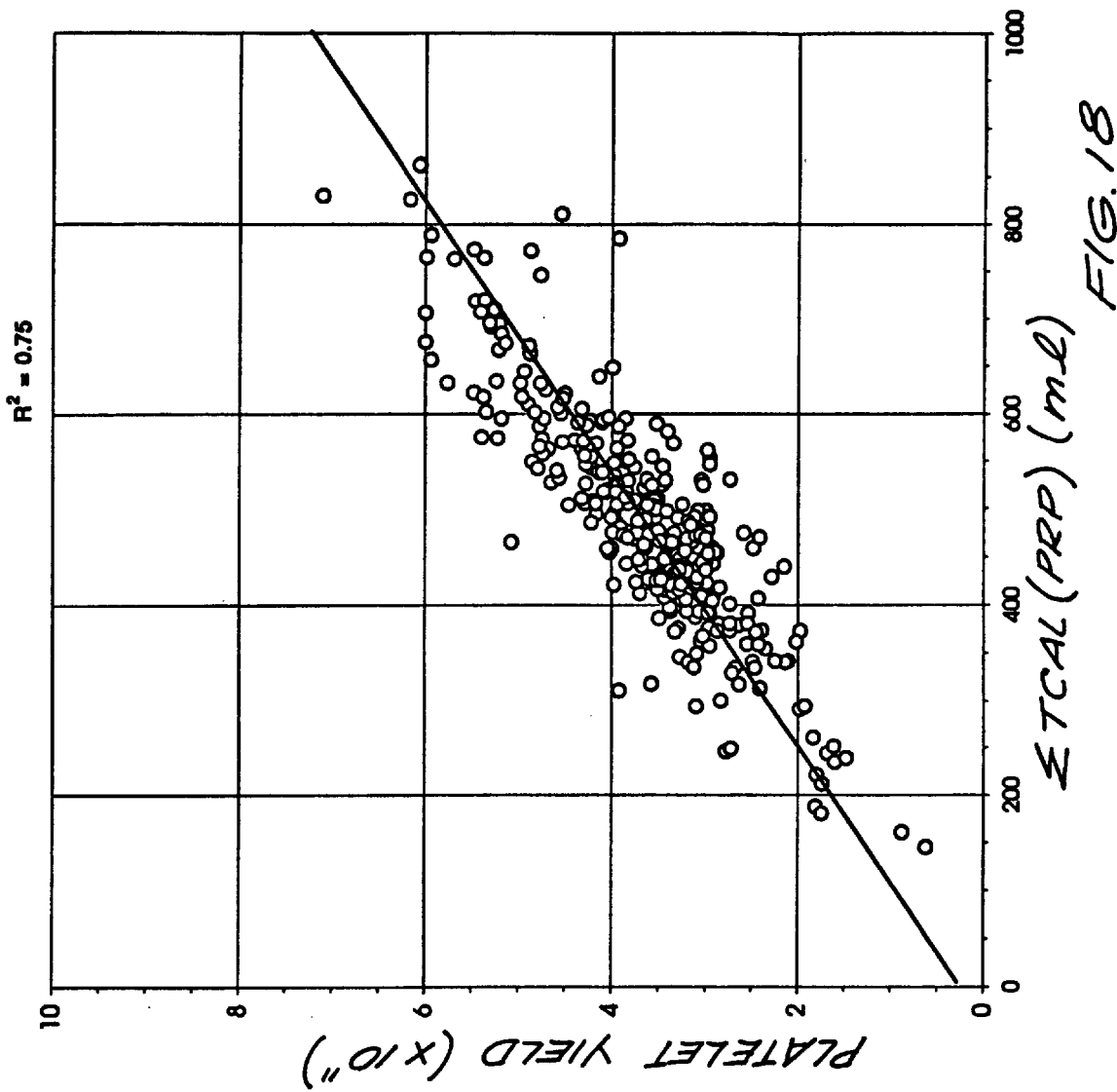
FIG. 18 is a plot showing the correlation of the integrated optical density value derived by the first utility function, shown in FIG. 15, to platelet yield data.

FIG. 18 shows a plot of the same 358 values of ΣTCAL (PRP) against associated platelet yields $PLT_{Yld}$ (expressed in units$\times 10^{11}$), which are derived by multiplying the platelet count (measured by an off line counter) by the volume of platelet concentrate. The plot shows a linear distribution having the following relationship:

$$PLT_{Yld}(\times 10^{11})=0.67+0.0080 \Sigma TCAL(PRP)$$

where the y-intercept of 0.67 is 17% of the nominal expected collected platelet volume of $4.0 \times 10^{11}$ ml. The linear distribution has an $r^2$ value of 0.70. FIG. 17 demonstrates that a correlation also exits between ΣTCAL(PRP) and platelet yields, but also illustrates that the quantity ΣTCAL(PRP) is more indicative of platelet volume $PLT_{Vol}$ than the number of platelets collected $PLT_{Yld}$.

Alternatively, the integrated value ΣTCAL(PRP) can be obtained by acquiring the value of T(PRP) at designated sample intervals during the platelet collection stage. T(PRP) can be adjusted for each sample interval by T(REDBKD) obtained either at the beginning of the processing period or during the designated sample interval. T(PRP) is also adjusted for each sample interval by a reference value T(REF) selected for T(PPP), which can be the optical transmission value of saline T(SAL) obtained during the set up procedure or an other selected reference value, adjusted by its background T(REFBKG) obtained at the beginning of the processing period. The value ΣTCAL(REF) can be derived from T(PRP) based upon T(REF), T(REDBKG), and T(REFBKG) during the platelet collection period and stored as a single value in memory 222.

The value of T(PPP) can be ascertained during the subsequent suspension stage and used to adjust the stored value of ΣTCAL(REF) to obtain ΣTCAL(PRP) as follows:

$$\sum TCAL(PRP) = \frac{T(REF)}{T(PPP)} \times \sum TCAL(REF) \qquad (7)$$

where both T(REF) and T(PPP) have been adjusted by T(REFBKG).

(2) Second Utility Function F2

The second utility function F2 includes a processing element 224 which receives as input the calculation of ΣTCAL(PRP) made by the first utility function F1. Based upon the value of ΣTCAL(PRP), the processing element 224 derives the optimum storage conditions to sustain the platelet volume collected during the expected storage period. The processing element 224 generates an output reflecting the number of preselected storage containers required for the platelets $Plt_{Bag}$ and the volume of plasma (PPP) $Plt_{Med}$ (in ml) to reside as a storage medium with the platelets.

The optimal storage conditions for platelets depends upon platelet volume desired to be stored $Plt_{Vol}$. As demonstrated above, the value of ΣTCAL(PRP) (in ml) correlates with $Plt_{Vol}$. Therefore, the platelet volume $Plt_{Vol}$ can be accurately expressed in terms of ΣTCAL(PRP), without the need to know the actual platelet yield or to independently assess platelet cell counts or mean platelet volumes (MPV).

As the value of ΣTCAL(PRP) increases, so too does the platelets' demand for oxygen during the storage period. As the value of ΣTCAL(PRP) increases, the platelets' glucose consumption to support metabolism and the generation of carbon dioxide and lactate as a result of metabolism also increase. The physical characteristics of the storage containers in terms of surface area, thickness, and material are selected to provide a desired degree of gas permeability to allow oxygen to enter and carbon dioxide to escape the container during the storage period.

The plasma storage medium contains bicarbonate $HCO_3$, which buffers the lactate generated by platelet metabolism, keeping the pH at a level to sustain platelet viability. As the value of ΣTCAL(PRP) increases, the demand for the buffer effect of $HCO_3$, and thus more plasma volume during storage, also increases.

A. Deriving $Plt_{Bag}$

Figure 19:
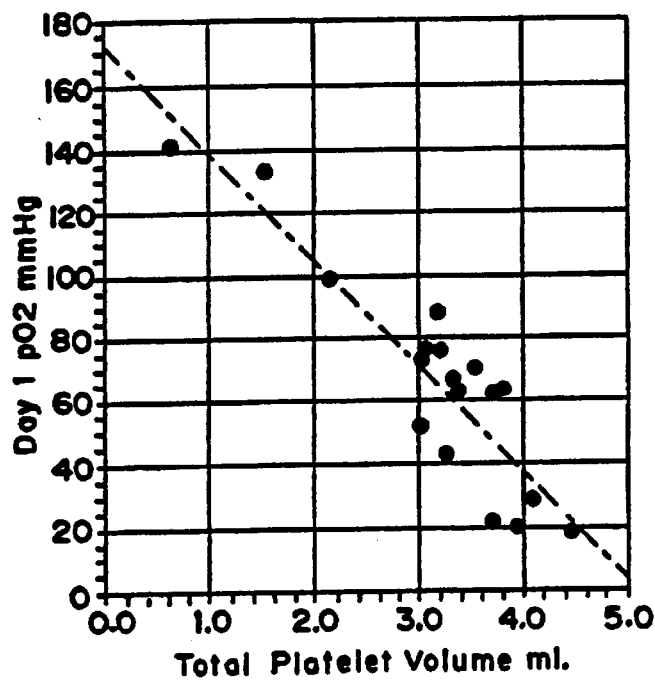
FIG. 19 is a graph showing the relationship between the partial pressure of oxygen and the permeation of a particular storage container, which the second utility function shown in FIG. 15 takes into account in recommending optimal storage parameters in terms of the number of storage containers.

The partial pressure of oxygen $pO_2$ (mmHg) of platelets stored within a storage container having a given permeation decreases in relation to the total platelet volume $Plt_{Vol}$ the container holds. FIG. 19 is a graph based upon test data showing the relationship between $pO_2$ measured after one day of storage for a storage container of given permeation. The storage container upon which FIG. 19 is based has a surface area of about 54 in² and a capacity of 1000 ml. The storage container has a permeability to $O_2$ of 194 cc/100 in²/day, and a permeability to $CO_2$ 1282 cc/100 in²/day.

When the partial pressure $pO_2$ drops below 20 mmHg, platelets are observed to become anaerobic, and the volume of lactate byproduct increases significantly. FIG. 19 shows that the selected storage container can maintain $pO_2$ of 40 mmHg (well above the aerobic region) at $Plt_{Vol} \leq 4.0$ ml. On this conservative basis, the 4.0 ml volume is selected as the target volume $Plt_{TVol}$ for this container. Target volumes $Plt_{TVol}$ for other containers can be determined using this same methodology.

The processing element 224 uses the target platelet volume $Plt_{TVol}$ to compute $Plt_{Bag}$ as follows:

$$BAG = \frac{a + b[\sum TCAL(PRP)]}{Plt_{TVol}} \qquad (8)$$

where:
a is the y-intercept and b is the slope of the plot between $PLT_{Vol}$ and ΣTCAL(PRP) derived by linear regression analysis, as previously described and shown in FIG. 17. The values of a and b will change according to the operating parameters of the particular blood processing system. In the illustrated embodiment a=0.24 and b=0.0070, and where $Plt_{Bag}$ is the number of storage containers required and:

$Plt_{Bag}=1$ when BAG≦1.0, otherwise $Plt_{Bag}=[BAG+1]$, where [BAG+1] is the integer part of the quantity BAG+1.

For example, based upon the systems upon which FIG. 17 is derived, given a value of ΣTCAL(PRP)=400 ml (which correlates to a $Plt_{Vol}=3.8$ ml), and given $Plt_{TVol}=4.0$ ml, BAG=0.95, and $Plt_{Bag}=1$. Based upon the systems upon which FIG. 17 is derived, if the value of ΣTCAL(PRP)=600 ml (which correlates to a $Plt_{Vol}=4.4$ ml), BAG=1.1 and $Plt_{Bag}=2$.

When $Plt_{Bag}>1$, the quantity a+bΣTCAL(PRP) is divided equally among the number of containers called for.

B. Deriving $Plt_{Med}$

The amount of bicarbonate used each day is a function of the storage thrombocytocrit Tct (%), which can be expressed as follows:

$$Tct = \frac{PLT_{Vol} \times MPV}{Plt_{Med}} \qquad (9)$$

Figure 20:
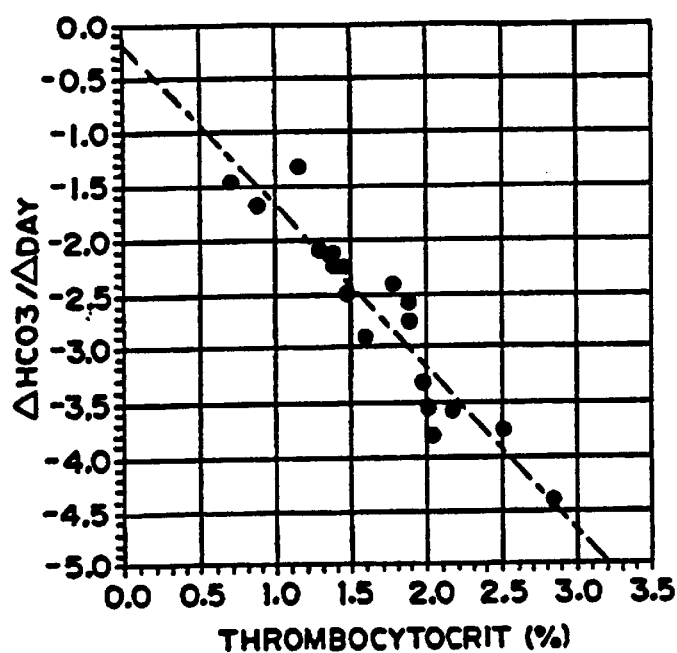
FIG. 20 is a graph showing the relationship between the consumption of bicarbonate and storage thrombocytocrit for a particular storage container, which the second utility function shown in FIG. 15 takes into account in recommending optimal storage parameters in terms of the volume of plasma storage medium.

The relationship between bicarbonate $HCO_3$ consumption per day and Tct can be empirically determined for the selected storage container. FIG. 20 shows a graph showing this relationship for the same container that the graph in FIG. 19 is based upon. The y-axis in FIG. 20 shows the empirically measured consumption of bicarbonate per day (in Meq/L) based upon Tct for that container. The processing element 224 includes the data expressed in FIG. 20, for example, in a look-up table 226.

The processing element 224 derives the anticipated decay of bicarbonate per day over the storage period $\Delta HCO_3$ as follows:

$$\Delta HCO_3 = \frac{Don_{HCO_3}}{Stor} \qquad (10)$$

where:
$Don_{HCO_3}$ is the measured bicarbonate level in the donor's blood (Meq/L), or alternatively, is the bicarbonate level for a typical donor, which is believed to be 19.0 Meq/L±1.3, and Stor is the desired storage interval (in days, typically between 3 to 6 days).

Given $\Delta HCO_3$, the processing element 224 derives Tct from the look-up table 226 for selected storage container. For the storage container upon which FIG. 20 is based, a Tct of about 1.35 to 1.5% is believed to be conservatively appropriate in most instances for a six day storage interval.

Knowing Tct and $\Sigma TCAL(PRP)$, the utility function F2 computes $Plt_{Med}$ based upon Eq (8), as follows:

$$Plt_{Med} = \frac{a + b[\sum TCAL(PRP)]}{\frac{Tct}{100}} \quad (11)$$

where Tct can be a value based upon empirical data for the particular storage container (as just described and shown in FIG. 20), and not requiring off line counting or sizing techniques.

When $Plt_{Bag} > 1$, $Plt_{Med}$ is divided equally among the number of containers called for.

Various features of the inventions are set forth in the following claims.

We claim:

1. A blood processing system comprising a separation chamber assembly operating to separate blood into constituents including a plasma constituent containing platelets and having a optical density, an outlet path for conveying a volume of the plasma constituent from the separation chamber assembly during a processing period, the volume of plasma constituent containing a platelet volume, a sensor assembly operating to detect the optical density of the plasma constituent in the outlet path during several sample intervals within the processing period and generate for each sample interval a sampled opacity value expressing the detected optical density as a function of incremental plasma volume processed during the respective sample interval, and a processing element coupled to the sensor assembly including an element that is operable to sum the sampled opacity values over the processing period and generate an integrated opacity value, the processing element including an output that expresses the platelet volume based upon the integrated opacity value.

2. A system according to claim 1 wherein the separation chamber assembly further separates the plasma constituent into a platelet-poor plasma constituent and a platelet concentrate comprising the platelet volume, the platelet-poor plasma constituent including an optical density that varies with lipid content, further including a sensor assembly operating to detect the optical density of the platelet-poor plasma constituent and generate a baseline optical density value, and wherein the processing element includes a calibration element that calibrates the integrated opacity value against the baseline optical density value.

3. A system according to claim 1 and further including a second processing element which receives as input the integrated opacity value and generates a second output based, at least in part, upon the integrated opacity value.

4. A system according to claim 3 wherein the second output comprises a parameter for storing the platelet volume.

5. A system according to claim 4 wherein the second output includes a value representing the number of selected storage containers to be used for the platelet volume.

6. A system according to claim 4 wherein the second output includes a value representing the recommended volume of storage medium for the platelet volume.

7. A system according to claim 1 wherein the sensor assembly includes an emitter of a selected wavelength of light energy and a detector of the selected wavelength.

8. A system according to claim 7 wherein the first output is free of side scatter effects.

9. A blood processing system comprising a separation chamber assembly operating to separate blood into constituents including a plasma constituent having an optical density, an outlet path for conveying a volume of the plasma constituent from the separation chamber assembly during a processing period, the volume of plasma constituent containing a platelet volume ($PLT_{Vol}$)(in ml), a sensor assembly operating to detect the optical density of the plasma constituent in the outlet path during several sample intervals (n) within the processing period and generate for each sample interval a sampled opacity value ($T_{(n)}$) expressing the detected optical density as a function of incremental plasma volume processed during the respective sample interval, and a processing element coupled to the sensor assembly including an element that is operable to sum the sampled opacity values ($T_{(n)}$) over the processing period and generate an integrated opacity output $\Sigma T$ that expresses the platelet volume ($PLT_{Vol}$) in relation to the integrated opacity output ($\Sigma T$) as a linear plot having a y-intercept (a) and a slope (b) as follows:

$$PLT_{Vol}(ml) = a + b[\Sigma T].$$

10. A system according to claim 9 wherein the separation chamber assembly further separates the plasma constituent into a platelet-poor plasma constituent and a platelet concentrate comprising the platelet volume ($PLTV_{Vol}$), the platelet-poor plasma constituent including an optical density that varies with lipid content, further including a sensor assembly operating to detect the optical density of the platelet-poor plasma constituent and generate a baseline optical density value, and wherein the processing element includes a calibration element that calibrates the integrated opacity output ($\Sigma T$) against the baseline optical density value.

11. A system according to claim 9 and further including a second processing element which receives as input the integrated opacity output ($\Sigma T$) and generates a second output, which includes a value representing the number of selected storage containers to be used for the platelet volume ($PLT_{VOL}$).

12. A system according to claim 11 wherein the second output includes a value representing the recommended volume of storage medium for the platelet volume.

13. A system according to claim 9 wherein the sensor assembly includes an emitter of a selected wavelength of light energy and a detector of the selected wavelength.

14. A system according to claim 13 wherein the first output is free of side scatter effects.

15. A blood processing method comprising separating blood into constituents including a plasma constituent containing platelets and having an optical density, conveying in an outlet path a volume of the separated plasma constituent during a processing period, the volume of separated plasma constituent containing a platelet volume, detecting the optical density of the plasma constituent in the outlet path during several sample intervals within the processing period, generating for each sample interval a sampled opacity value expressing the detected optical density as a function of incremental plasma volume processed during the respective sample interval, generating an integrated opacity value by summing the sampled opacity values over the processing period, and expressing the platelet volume based upon the integrated opacity value.

16. A method according to claim 15 wherein the separating step provides a platelet-poor plasma constituent which includes an optical density that varies with lipid content, further including the steps of detecting the optical density of the platelet-poor plasma constituent and generate a baseline optical density value and calibrating the integrated opacity value against the baseline optical density value.

17. A method according to claim 15 and further including the step of generating an output based, at least in part, upon the integrated opacity value.

18. A method according to claim 17 wherein the output comprises a parameter for storing the platelet volume.

19. A method according to claim 18 wherein the output includes a value representing the number of selected storage containers to be used for the platelet volume.

20. A method according to claim 18 wherein the output includes a value representing the recommended volume of storage medium for the platelet volume.

21. A method according to claim 15 wherein the step of generating the sampled opacity values is free of side optical scatter effects.

22. A blood processing system comprising a separation chamber assembly operating to separate blood into a platelet-rich plasma constituent containing platelets and having a first optical density, and then separates the platelet-rich plasma constituent into a platelet concentrate and a platelet-poor plasma constituent having a second optical density, a sensor assembly operating to detect the first optical density and generate a first output indicative of the first optical density, a sensor assembly operating to detect the second optical density and generate a second output indicative of the second optical density, and a processing element coupled to each sensor assembly including an element that is operable to calibrate the first output against the second output to derive a calibrated opacity value which reflects the opacity of the platelet-rich plasma constituent due solely to platelets contained therein, the processing element further including an element that is operable to integrate the calibrated opacity value relative to a volume of platelet-rich plasma constituent processed over a time interval and generate an integrated output that expresses volume of platelets contained in the platelet concentrate processed during the time interval.

23. A system according to claim 22 wherein the sensor assembly to detect the first optical density and the sensor assembly to detect the second optical density comprise a single sensing element.

24. A system according to claim 22 and further including a second processing element which receives as input the integrated output and generates a third output based, at least in part, upon the integrated output comprising a parameter for storing the platelet concentrate.

25. A system according to claim 24 wherein the parameter includes a value representing the number of selected storage containers to be used for the platelet concentrate.

26. A system according to claim 24 wherein the parameter includes a value representing the recommended volume of storage medium for the platelet concentrate.

27. A blood processing method comprising the steps of separating blood into a platelet-rich plasma constituent containing platelets and having a first optical density, separating the platelet-rich plasma constituent into a platelet concentrate and a platelet-poor plasma constituent having a second optical density, detecting the first optical density to generate a first output indicative of the first optical density, detecting the second optical density to generate a second output indicative of the second optical density, calibrating the first output against the second output to derive a calibrated opacity value which reflects the opacity of the platelet-rich plasma constituent due to platelets contained therein, and integrating the calibrated opacity value relative to a volume of platelet-rich plasma constituent processed over a time interval to generate an integrated output that expresses volume of platelets contained in the platelet concentrate processed during the time interval.

28. A method according to claim 27 further including the step of generating a parameter for storing the platelet concentrate based, at least in part, upon the integrated output.

29. A method according to claim 28 wherein the parameter includes a value representing the number of selected storage containers to be used for the platelet concentrate.

30. A method according to claim 28 wherein the parameter includes a value representing the recommended volume of storage medium for the platelet concentrate.

* * * * *